US008198252B2

(12) United States Patent
Evans et al.

(10) Patent No.: US 8,198,252 B2
(45) Date of Patent: Jun. 12, 2012

(54) SIRNA INHIBITION OF PI3K P85, P110, AND AKT2 AND METHODS OF USE

(75) Inventors: B. Mark Evans, Galveston, TX (US); Piotr G. Rychahou, Galveston, TX (US)

(73) Assignee: Board of Regents, The University of Texas System, Austin, TX (US)

( * ) Notice: Subject to any disclaimer, the term of this patent is extended or adjusted under 35 U.S.C. 154(b) by 0 days.

(21) Appl. No.: 12/301,387

(22) PCT Filed: May 18, 2007

(86) PCT No.: PCT/US2007/011917
§ 371 (c)(1),
(2), (4) Date: Sep. 21, 2009

(87) PCT Pub. No.: WO2007/136758
PCT Pub. Date: Nov. 29, 2007

(65) Prior Publication Data
US 2010/0035965 A1    Feb. 11, 2010

Related U.S. Application Data

(60) Provisional application No. 60/801,729, filed on May 19, 2006.

(51) Int. Cl.
*C12N 15/11* (2006.01)
(52) U.S. Cl. .................................................. 514/44 A
(58) Field of Classification Search ................. 514/44 A
See application file for complete search history.

(56) References Cited

U.S. PATENT DOCUMENTS

| | | | |
|---|---|---|---|
| 6,043,090 A * | 3/2000 | Monia et al. ................... | 435/375 |
| 6,194,389 B1 | 2/2001 | Johnston et al. | |
| 7,410,988 B2 | 8/2008 | Dickson, Jr. et al. | |
| 7,622,271 B2 | 11/2009 | Kennedy et al. | |
| 2002/0150541 A1 | 10/2002 | Lau et al. | |
| 2003/0135033 A1 | 7/2003 | Klippel-Giese et al. | |
| 2004/0198640 A1 | 10/2004 | Leake et al. | |
| 2005/0255487 A1* | 11/2005 | Khvorova et al. ................ | 435/6 |
| 2005/0287128 A1 | 12/2005 | Guerciolini et al. | |
| 2005/0287544 A1 | 12/2005 | Bertucci et al. | |
| 2007/0004667 A1 | 1/2007 | McSwiggen et al. | |
| 2008/0063637 A1* | 3/2008 | Tsichlis et al. ............. | 424/130.1 |

OTHER PUBLICATIONS

Roy et al. (Carcinogenesis, 23: 201-205, 2002).*
Takeuchi et al. (Clin. Cancer Res. 2005 11, 7621-7628).*
Arboleda et al., "Overexpression of AKT2/Protein Kinase Bβ Leads to Up-Regulation of β1 Integrins, Increased Invasion, and Metastatis of Human Breast and Ovarian Cancer Cells," *Cancer Res.*, Jan. 1, 2003;63:196-206.
Asano et al., "The PI 3-kinase/Akt signaling pathway is activated due to aberrant Pten expression and targets transcription factors NF-κb and c-Myc in pancreatic cancer cells," *Oncogene*, 2004;23(53):8571-8580.
Barone et al. "Polymorphonuclear leukocyte infiltration into cerebral focal ischemic tissue: myeloperoxidase activity assay and histologic verification," *Journal of Neuroscience Research*, 1991;29:336-345.
Bellacosa et al., "A Retroviral Oncogene, Akt, Encoding A Serine-Threonine Kinase Containing an Sh2-Like Region," *Science*, 1991;254(5029):274-277.
Birmingham et al., "3' UTR seed matches, but not overall identity, are associated with RNAi off-targets," *Nature Methods*, Mar. 2006;3(3):199-204.
Blume-Jensen et al., "Oncogenic kinase signalling," *Nature*, 2001;411:355-365.
Bradford, "A rapid and sensitive method for the quantitation of microgram quantities of protein utilizing the principle of protein-dye binding," *Anal. Biochem.*, 1976;72:248-254.
Bruns et al., "In Vivo Selection and Characterization of Metastatic Variants from Human Pancreatic Adenocarcinoma by Using Orthotopic Implantation in Nude Mice," *Neoplasia*, 1999;1(1):50-62.
Cai et al., "Mitochondrial control of apoptosis: the role of cytochrome c," *Biochimica et Biophysica Acta (BBA)-Bioenergetics*, Aug. 10, 1998;1366(1-2):139-149.
Campbell et al., "Mutation of the *PIK3CA* Gene in Ovarian and Breast Cancer," *Cancer Res.*, Nov. 1, 2004;64:7678-7681.
Cantley et al., "New insights into tumor suppression: PTEN suppresses tumor formation by restraining the phosphoinositide 3-kinase/AKT pathway," *Proc. Natl. Acad. Sci. USA*, Apr. 1999;96:4240-4245.
Cantley, "The Phosphoinositide 3-Kinase Pathway," *Science*, 2002;296:1655-1657.
Caplen et al., "Specific inhibition of gene expression by small double-stranded RNAs in invertebrate and vertebrate systems," *Proc. Natl. Acad. Sci. USA*, Aug. 14, 2001;98(17):9742-9747.
Carpenter et al., "Phosphoinositide kinases," *Curr. Opin. Cell Biol.*, 1996;8:153-158.
Chan et al., "Phase II Study of Temsirolimus (CCI-779), a Novel Inhibitor of mTOR, in Heavily Pretreated Patients with Locally Advanced or Metastic Breast Cancer," *J Clin. Oncol.*, 2005;23(23):5314-5322.
Chiu et al., "siRNA function in RNAi: a chemical modification analysis," *RNA*, 2003;9(9):1034-1048.
Datta et al., "Akt phosphorylation of BAD couples survival signals to the cell-intrinsic death machinery," *Cell*, Oct. 17, 1997;91(2):231-241.
Davies et al., "Specificity and mechanism of action of some commonly used protein kinase inhibitors," *Biochem. J.*, 2000;351:95-105.
Di Cristofano et al., "*Pten* is essential for embryonic development and tumour suppression," *Nature Genetics*, 1998;19(4):348-355.
Elbashir et al., "RNA interference is mediated by 21-and 22-nucleotide RNAs," *Genes & Development*, 2001;15:188-200.
Evers, "Small Bowel," *Sabiston Textbook of Surgery*, ed. Townsend, Saunders, Philadelphia, PA, 16th edition, 2001, Chapter 44:888-897.
Fresno Vara et al., "PI3K/Akt signalling pathway and cancer," *Cancer Treatment Reviews*, 2004;30(2):193-204.

(Continued)

*Primary Examiner* — Brian Whiteman
(74) *Attorney, Agent, or Firm* — Mueting, Raasch & Gebhardt, P.A.

(57) ABSTRACT

The present invention provides polynucleotides, compositions including polynucleotides, and the uses thereof for treating cancer in a subject. The polynucleotides silence the expression of coding regions that encode polypeptides such as p85α, p110α, and Akt2. The cancers treatable using the methods described herein include colorectal cancer, breast cancer, lung cancer, and metastases thereof.

10 Claims, 6 Drawing Sheets

OTHER PUBLICATIONS

Fruman et al., "Phosphoinositide Kinases," *Ann. Rev. Biochem.*, 1998;67(1):481-507.

Gershtein et al., "Phosphatidylinositol 3-kinase expression in human breast cancer," *Clinica Chimica Acta*, 1999;287(1-2):59-67.

Glickman, "Inflammatory Bowel Disease: Ulcerative Colitis and Crohn's Disease," *Harrison's Principles of Internal Medicine*, ed. AS Fauci., McGraw-Hill, New York, NY, 14th edition, 1998; chapter 286:1633-1645.

Goel et al., "Frequent Inactivation of PTEN by Promoter Hypermethylation in Microsatellite Instability-High Sporadic Colorectal Cancers," *Cancer Res.*, May 1, 2004;64(9):3014-3021.

Green et al., "The central executioners of apoptosis: caspases or mitochondria?" *trends in Cell Biology*, Jul. 1998;8(7):267-271.

Green et al., "Mitochondria and Apoptosis," *Science*, Aug. 28, 1998;281(5381):1309-1312.

Gröttup-Wolfers et al., "Elevated cell-associated levels of interleukin 1β and interleukin 6 in inflamed mucosa of inflammatory bowel disease," *European Journal of Clinical Investigation*, 1996;26:115-122.

Guanti et al., "Involvement of *PTEN* mutations in the genetic pathways of colorectal cancerogenesis," *Human Molecular Genetics*, 2000;9(2):283-287.

Guha et al., "LPS induction of gene expression in human monocytes," *Cellular Signalling*, 2001;13:85-94.

Gunther et al., "Acute pathological effects on rats of orally administered wortmannin-containing preparations and puffed wortmarmin from *fusarium oxysporum*," *Food Chem. Toxicol.*, 1989;27(3):173-179.

Hamajima et al., "Intranasal Administration of HIV-DNA Vaccine Formulated with a Polymer, Carboxymethylcellulose, Augments Mucosal Antibody Production and Cell-Mediated Immune Response," *Clinical Immunology and Immunopathology*, 1998;88(2):205-210.

Hernandez et al., "Sensitization of human colon cancer cells to TRAIL-mediated apoptosis," *Journal of Gastrointestinal Surgery*, Jan./Feb. 2001;5:56-65.

Hernandez et al., "Butyrate sensitizes human colon cancer cells to TRAIL-mediated apoptosis," *Surgery*, Aug. 2001;130(2):265-272.

Hirsch et al., "Central Role for G Protein-Coupled Phosphoinositide 3-Kinase γ in Inflammation," *Science*, Feb. 11, 2000;287(5455):1049-1053.

Hortobagyi, "Developments in Chemotherapy of breast cancer," *Cancer*, 2000;88(12 Suppl):3073-3079.

Hutchinson et al., "Activation of Akt-1 (PKB-α) Can Accelerate ErbB-2-Mediated Mammary Tumorigenesis but Suppresses Tumor Invasion," *Cancer Res.*, May 1, 2004;64(9):3171-3178.

Ikenoue et al., "Functional Analysis of PIK3CA Gene Mutations in Human Colorectal Cancer," *Cancer Res.*, Jun. 1, 2005;65(11):4562-4567.

Insinga et al., "Inhibitors of histone deacetylases induce tumor-selective apoptosis through activation of the death receptor pathway," *Nature Medicine*, 2005;1 1:71- 76.

Itoh et al., "Phosphorylation of Akt/Pkb is Required for Suppression of Cancer Cell Apoptosis and Tumor Progression in Human Colorectal Carcinoma," Cancer, Jun. 15, 2002;94(12):3127-3134.

Iwase et al., "Inhibition of Neurotensin-Induced Pancreatic Carcinoma Growth by a Nonpeptide Neurotensin Receptor Antagonist, SR48692," *Cancer*, May 1, 1997; 79(9):1787-1793.

Jacque et al., "Modulation of HIV-1 replication by RNA interference," *Nature*, 2002;418:435-438.

Jemal et al., "Cancer Statistics, 2003" *CA Cancer J. Clin.*, 2003;53(1):5-26.

Jimenez et al., "Identification and characterization of a new oncogene derived from the regulatory subunit of phosphoinositide 3-kinase," *EMBO J.*, 1998;17(3):743-753.

Jimenez et al., "The p85 Regulatory Subunit Controls Sequential Activation of Phosphoinositide 3-Kinase by Tyr Kinases and Ras," *J Biol. Chem.*, Nov 1, 2002;277(44):41556-41562.

Kandasamy et al., "Role of the Phosphatidylinositol 3'-Kinase/ PTEN/Akt Kinase Pathway in Tumor Necrosis Factor-related Apoptosis-inducing Ligand-induced Apoptosis in Non-Small Cell Lung Cancer Cells," *Cancer Research*, Sep. 2002;62(17):4929-4937.

Kapiteijn et al., "Mechanisms of oncogenesis in colon versus rectal cancer," *The Journal of Pathology*, Sep. 2001:195(2):171-178.

Karakas et al., "Mutation of the *PIK3CA* oncogene in human cancers," *British Journal of Cancer*, 2006;94:455-459.

Katome et al., "Use of RNA Interference-mediated Gene Silencing and Adenoviral Overexpression to Elucidate the Roles of AKT/Protein Kinase B Isoforms in Insulin Actions," *J. Bio. Chem.*, Jul. 25, 2003;278(30):28312-28323.

Khaleghpour et al., "Involvement of the PI 3-kinase signaling pathway in progression of colon adenocarcinoma," *Carcinogenesis*, 2004;25(2):241-248.

Kim et al., "Divergent Regulation of Akt1 and Akt2 Isoforms in Insulin Target Tissues of Obese Zucker Rats," *Diabetes*, May 2000;49:847-856.

Kim et al., "Current status of the molecular mechanisms of anticancer drug-induced apoptosis: The contribution of molecular-level analysis to cancer chemotherapy," *Cancer Chemother. Pharmacol.*, 2002;50(5):343-352.

Kim et al., "*PTEN* and TNF-α regulation of the intestinal-specific *Cdx-2* homeobox gene through a PI3K, PKB/Akt, and NF-κB-dependent pathway," *Gastroenterology*, 2002;123(4):1163-1178.

Krystal et al., "Inhibition of Phosphatidylinositol 3-Kinase-Akt Signaling Blocks Growth, Promotes Apoptosis, and Enhances Sensitivity of Small Cell Lung Cancer Cells to Chemotherapy," *Mol. Cancer Ther.*, Sep. 2002;1(11):913-922.

Kuriyama et al., "Electrochemotherapy can eradicate established colorectal carcinoma and leaves a systemic protective memory in mice," *International Journal of Oncology*, 2000; 16(5):979-985.

Li et al., "PTEN, a putative protein tyrosine phosphatase gene mutated in human brain, breast, and prostate cancer," *Science*, 1997;275(5308):1943-1947.

Lin et al., "siRNA-mediated off-target gene silencing triggered by a 7 nt complementation," *Nucl. Acids Res.*, 2005;33(14):4527-4535.

Liu et al., "Rapamycin inhibits Akt-mediated oncogenic transformation and tumor growth," *Anticancer Res.*, 2004;24:2697-2704.

Lundstrom et al., "Viral and non-viral vectors in gene therapy technology development and clinical trials.," *Technology in Cancer Research & Treatment*, 2003;2(5):471-485.

Macdonald et al., "A molecular gradient in early *Drosophila* embryos and its role in specifying the body pattern," *Nature*, 1986;324(6097):537-545.

Marques et al., "A structural basis for discriminating between self and nonself double-stranded RNAs in mammalian cells," *Nat. Biotech.*, 2006;24(5):559-565.

Matzke et al., "RNAi-mediated pathways in the nucleus," *Nat. Rev. Genet.*, 2005;6(1):24-35.

Maurer et al., "Apoptosis inhibiting factor Bcl-$x_L$ might be the crucial member of the *Bcl-2* gene family in colorectal cancer," *Digestive Diseases and Sciences*, Dec. 1998;43(12):2641-2648.

Micke et al., "Exploring the tumour environment: cancer-associated fibroblasts as targets in cancer therapy," *Expert Opin. Ther. Targets*, 2005;9(6):1217-1233.

Morikawa et al., "In Vivo Selection of Highly Metastatic Cells from Surgical Specimens of Different Primary Human Colon Carcinomas Implanted into Nude Mice," *Cancer Res.*, Apr. 1, 1988;48:1943-1948.

Morikawa et al., "Influence of Organ Environment on the Growth, Selection, and Metastasis of Human Colon Carcinoma Cells in Nude Mice," *Cancer Res.*, Dec. 1, 1988;48:6863-6871.

Mortier et al., "Nuclear speckles and nucleoli targeting by $PIP_2$-PDZ domain interactions," *EMBO J.*, 2005;24:2556-2565.

Murano et al., "Therapeutic effect of intracolonically administered nuclear factor κB (p65) antisense oligonucleotide on mouse dextran sulphate sodium (DSS)-induced colitis," *Clinical and Experimental Immunology*, 2000;120:51-58.

Murillo et al., "Inhibition of α5 integrin decreases PI3K activation and cell adhesion of human colon cancers," *Surgery*, 2004;136(2): 143-149.

Murthy et al., "Treatment of dextran sulfate sodium-induced murine colitis by intracolonic cyclosporin," *Digestive Diseases and Sciences*, Sep. 1993;38(9):1722-1734.

Natarajan et al., "Hypoxia Inducible Factor-1 Activation by Prolyl 4-Hydroxylase-2 Gene Silencing Attenuates Myocardial Ischemia Reprefusion Injury," *Circ. Res.*, 2006;98(1):133-140.

National Center for Biotechnology Information, National Library of Medicine, National Institutes of Health, Accession No. NM_181523, "*Homo sapiens* phosphoinositide-3-kinase, regulatory subunit 1 (p85 alpha) (PIK3R1), transcript variant 1, mRNA," [online]. Bethesda, MD [retrieved on May 18, 2007]. Retrieved from the Internet<URL:www.ncbi.nlin.nih.gov/entrea/viewer.fcgi?db=nucleotide&val=32455247>; 6 pgs.

National Center for Biotechnology Infottnation, National Library of Medicine, National Institutes of Health, Accession No. NM_181504, "*Homo sapiens* phosphoinositide-3-kinase, regulatory subunit 1 (p85 alpha) (PIK3R1), transcript variant 2, mRNA" [online]. Bethesda, MD [retrieved on May 18, 2007]. Retrieved from the Internet<URL:www.ncbi.nlin.nih.gov/entrea/viewer.fcgi?db=nucleotide&val=32455251>; 6 pgs.

National Center for Biotechnology Information, National Library of Medicine, National Institutes of Health, Accession No. NM_181524, "*Homo sapiens* phosphoinositide-3-kinase, regulatory subunit 1 (p85 alpha) (PIK3R1), transcript variant 3, mRNA," [online]. Bethesda, MD [retrieved on May 18, 2007]. Retrieved from the Internet<URL:-www.ncbi.nlm.nih.gov/entrea/viewer.fcgi?db=nucleotide&val=32455249>; 6 pgs.

National Center for Biotechnology Information, National Library of Medicine, National Institutes of Health, Accession No. NM_006218, "*Homo sapiens* phosphoinositide-3-kinase, catalytic, alpha polypeptide (PIK3CA), mRNA," [online]. Bethesda, MD [retrieved on May 18, 2007]. Retrieved from the Internet<URL:www.ncbi.nlm.nih.gov/entrea/viewer.fcgi?db=r mcleotide&val=54 792081>; 5 pgs.

National Center for Biotechnology Information, National Library of Medicine, National Institutes of Health, Accession No. NM_001626, "*Homo sapiens* v-akt murine thymoma viral oncogene homolog 2 (AKT2), mRNA," [online]. Bethesda, MD [retrieved on May 18, 2007]. Retrieved from the Internet:<URL: www.ncbi.nlm.nih.gov/entrea/viewer.fcgi?db=nucleotide&val=126273601>; 5 pgs.

National Center for Biotechnology Infounation, National Library of Medicine, National Institutes of Health, Accession No. NP_001617, "v-akt murine thymoma viral oncogene homolog 2 (*Homo sapiens*), mRNA," [online]. Bethesda, MD [retrieved on May 18, 2007]. Retrieved from the Internet:<URL:www.ncbi.nlm.nih.gov/entrea/viewer.fcgi?db=nucleotide&val=4502023>; 4 pgs.

National Center for Biotechnology Infoimation, National Library of Medicine, National Institutes of Health, Accession No. NM_005163, "*Homo sapiens* v-akt murine thymoma viral oncogene homolog 1 (AKT1), transcript variant 1, mRNA," [online]. Bethesda, MD [retrieved on Sep. 9, 2010]. Retrieved from the Internet<URL:www.ncbi.nlm.nih.gov/nuccore/62241010>; 4 pgs.

National Center for Biotechnology Information, National Library of Medicine, National Institutes of Health, Accession No. NM_019884, "*Homo sapiens* glycogen synthase kinase 3 alpha (GSK3A), mRNA," [online]. Bethesda, MD [retrieved on Sep. 3, 2010]. Retrieved from the Internet<URL:www.ncbi.nlm.nih.gov/nuccore/49574531>; 4 pgs.

Ng et al., "Wortmannin Inhibits PKB/Akt Phosphorylation and Promotes Gemcitabine Antitumor Activity in Orthotopic Human Pancreatic Cancer Xenografts in Immunodeficient Mice," *Clin. Cancer Res.*, Oct. 2001;7:3269-3275.

Nicholson et al., "The protein kinase B/Akt signalling pathway in human malignancy," *Cellular Signalling*, 2002;14(5):381-395.

Nieth et al., "Modulation of the classical multidrug resistance (MDR) phenotype by RNA interference (RNAi)," *FEBS Letters*, 2003;545:144-150.

Okkenhaug et al., "New Responsibilities for the PI3K Regulatory Subuiiit p85α," *Science 's stke*, Jan. 2001 (65); pel.

Okkenhaug et al., "Impaired B and T cell antigen receptor signaling in p110δ PI 3-kinase mutant mice," *Science*, Aug. 9, 2002;297(5583):1031-1034.

Osaki et al., "PI3K-Aid pathway; Its functions and alterations in human cancer," *Apoptosis*, 2004;9(6):667-676.

Osawa et al., "Tumor Necrosis Factor Alpha-Induced Interleukin-8 Production via NF-κb and Phosphatidylinositol 3-Kinase/Akt Pathways Inhibits Cell Apoptosis in Human Hepatocytes," *Infection and Immunity*, Nov. 2002;70(11):6294-6301.

Paddison et al., "Short hairpin RNAs (shRNAs) induce sequence-specific silencing in mammalian cells," *Genes & Development*, 2002;16:948-958.

Page et al., "Overexpression of Akt/AKT can modulate chemotherapy-induced apoptosis," *Anticancer Research*, 2000;20(1A):407-416.

Pan et al. "An antagonist decoy receptor and a death domain-containing receptor for TRAIL," Science, 8 Aug. 1997;277:815-818.

Pei et al., "On the art of identifying effective and specific siRNAs," *Nature Methods*, 2006;3(9):670-676.

Phillips et al., "Increased Levels of Phosphatidylinositol 3-Kinase Activity in Colorectal Tumors," *Cancer*, 1998;83(1):41-47.

Philp et al., "The Phosphatidylinositol 3'kinase p85α Gene is an Oncogene in Human Ovarian and Colon Tumors," Cancer Res., Oct. 15, 2001;61(20):7426-7429.

Powis et al., "Wollutannin, a Potent and Selective Inhibitor of Phosphatidylinositol-3-kinase," *Cancer Res.*, May 1, 1994;54:2419-2423.

Qiu et al., "A computational study of off-target effects of RNA interference," *Nucl. Acids Res.*, 2005;33(6):1834-1847.

Raymond et al., "Safety and Pharmacokinetics of Escalated Doses of Weekly Intravenous Infusion of CCI-779, a Novel mTOR Inhibitor, in Patients with Cancer," *J. Clin. Oncol.*, Jun. 15, 2004;22(12):2336-2347.

Ren et al., "Phosphatidylinositol 3-kinase p85αSubunit-Dependent Interaction with BCR/ABL-Related Fusion Tyrosine Kinases: Molecular Mechanisms and Biological Consequences," *Mol. Cell. Biol.*, Sep. 2005;25(18):8001-8008.

Rose et al., "Functional polarity is introduced by Dicer processing of short substrate RNAs," *Nucleic Acids Research*, 2005;33(13):4140-4156.

Roy et al., "AKT proto-oncogene overexpression is an early event during sporadic colon carcinogenesis," *Carcinogenesis*, 2002;23(1):201-205.

Ruemmele et al., "Butyrate induced Caco-2 cell apoptosis is mediated via the mitochondrial pathway," *Cancer*, 2003;52:94-100.

Rush et al., "Immunoaffinity profiling of tyrosine phosphorylation in cancer cells," *Nature Biotechnology*, 2005;23(1):94-101.

Rychahou et al., "Targeted RNA interference of PI3K pathway components sensitizes colon cancer cells to Tnf-related apoptosis-inducing ligand (TRAIL)," *Surgery*, 2005;138(2):391-397.

Rychahou et al., "Targeted Molecular Therapy of the PI3K Pathway: *Therapeutic Significance of PI3K Subunit Targeting in Colorectal Carcinoma*," Annals of Surgery, Jun. 2006;243:833-844.

Rychahou et al., "Akt2 overexpression plays a critical role in the establishment of colorectal cancer metastasis," *PNAS*, Dec. 2008; 105(50:20315-20320.

Salvesen et al., " Caspases: intracellular signaling by proteolysis," *Cell*, Nov. 14, 1997;91(4):443-446.

Sambrook et al., *Molecular Cloning: A Laboratory Manual, Books 1-3*, Cold Spring Harbor Laboratory Press, Cold Spring Harbor, NY, 1989; title page, publisher's page and table of contents only (30) pgs.

Samuels et al., "Mutant PIK3CA promotes cell growth and invasion of human cancer cells," *Cancer Cell*, 2005;7(6):561-573.

Semba et al., "Down-Regulation of *PIK3CG*, a Catalytic Subunit of Phophatidylinositol 3-OH Kinase, by CpG Hypermethylation in Human Colorectal Carcinoma," *Clin Cancer Res.*, 2002;8:3824-3831.

Semba et al., "The in Vitro and in Vivo Effects of 2-(4-Morpholinyl)-8-phenylchromone (LY294002), a Specific Inhibitor of Phosphatidylinositol 3'-Kinase, in Human Colon Cancer Cells," *Clin. Cancer Res.*, Jun. 2002;8:1957-1953.

Shao et al., "Roles of Phosphatidylinositol 3'-Kinase and Mammalian Target of Rapamycin/p70 Ribosomal Protein S6 Kinase in K-Ras-Mediated Transformation of Intestinal Epithelial Cells," *Cancer Res.*, Jan. 1, 2004;64(1):229-235.

Sioud et al., "Cationic liposome-mediated delivery of siRNAs in adult mice," *Biochemical and Biophysical Research Communication*, 2003;312:1220-1225.

Skehan et al., "New Colorimetric Cytotoxicity Assay for Anticancer-Drug Screening," *J. Natl. Cancer Inst.*, 1990;82(13):1107-1112.

Song et al. "RNA interference targeting Fas protects mice from fulminant hepatitis," *Nat. Med.*, 2003;9(3):347-351.

Sørenson et al., "Gene silencing by systemic delivery of synthetic siRNAs in adult mice," *J. Mol. Biol.*, Apr. 4, 2003;327(4):761-766.

Sui et al., "A DNA vector-based RNAi technology to suppress gene expression in mammalian cells," *Proc. Natl. Acad. Sci. USA*, Apr 16, 2002;99(8):5515-5520.

Takeshita et al., "Efficient delivery of small interfering RNA to bone-metastic tumors by using atelocollagen in vivo," *Proc. Natl. Acad. Sci. USA*, Aug. 23, 2005;102(34):12177-12182.

Tao et al., "Inhibiting the growth of malignant melanoma by blocking the expression of vascular endothelial growth factor using an RNA interference approach," *British J. Dermatol.*, 2005;153(4):715-724.

Tessner et al., "Prostaglandins prevent decreased epithelial cell proliferation associated with dextran sodium sulfate injury in mice," *Gastroenterology*, Oct. 1998;115(4):874-882.

Thomas et al., "Selective targeting of the nuclear factor-κb pathway enhances tumor necrosis factor-related apoptosis-inducing ligand-mediated pancreatic cancer cell death," *Surgery*, Aug. 2002;132:127-134.

Uchida et al., "Adenovirus-Mediated Transfer of siRNA against Survivin Induced Apoptosis and Attenuated Tumor Cell Growth in Vitro and in Vivo," *Molecular Therapy*, 2004;10(1):162-171.

Ueki et al., "Positive and Negative Regulation of Phosphoinositide 3-Kinase-Dependent Signaling Pathways by Three Different Gene Products of the p85α Regulatory Subunit," *Mol. Cell Biol.*, Nov. 2000;20(21):8035-8046.

Vanhaesebroeck B, "Signaling by Distinct Classes of Phosphoinositide 3-Kinases," *Exper. Cell Res.*, 1999;253(1):239-254.

Wang et al., "Downregulation of mitogen-activated protein kinases in human colon cancers," *Anticancer Research*, 2000;20:75-84.

Wang et al., "Augmentation of Sodium Butyrate-induced Apoptosis by Phosphatyidylinositol 3'-Kinase Inhibition in the KM20 Human Colon Cancer Cell Line," *Clin. Cancer Res.*, Jun. 2002;8:1940-1947.

Watanabe et al., "Aging is associated with decreased pancreatic acinar cell regeneration and phosphatidylinositol 3-kinase/Akt activation," *Gastroenterology*, 2005;128(5):1391-1404.

Wyllie et al., "Cell Death: the significance of apoptosis," *International Review of Cytology*, 1980;68:251-306.

Yin et al., "siRNA Agents inhibit oncogene expression and attenuate human tumor cell growth," *J. Exp. Therapeutics*, 2003;3:194-204.

Yu et al., "Regulation of the p85/p110 Phosphatidylinositol 3'-Kinase: Stabilization and Inhibition of the p110α Catalytic Subunit by the p85 Regulatory Subunit," *Mol. Cell. Biol.*, Mar. 1998;18(3):1379-1387.

Zhang et al., "High levels of foreign gene expression in hepatocytes after tail vein injections of naked plasmid DNA," *Human Gene Ther.*, 1999;10:1735-1737.

Zhang et al., "Tumor Growth Inhibition by Simultaneously Blocking Epideinial Growth Factor Receptor and Cyclooxygenase-2 in a Xenograft Model," *Clin. Cancer Res.*, Sep. 1, 2005;11(17):6261-6269.

Zheng et al., "Caspase-3 controls both cytoplasmic and nuclear events associated with Fas-mediated apoptosis in vivo," *PNAS*, Nov. 10, 1998;95(23):13618-13623.

International Preliminary Report on Patentability and Written Opinion for PCT/US2007/011917; 8 pgs.

International Search Report for PCT/US2007/011917; 4 pgs.

Altomare et al., "Perturbations of the AKT signaling pathway in human cancer," *Oncogene*, 2005; 24:7455-7464.

Chau et al., "Akt2: a role in breast cancer metastasis," *Breast Cancer Res.*, 2004; 6:55-57.

Cheng et al., "AKT2, a putative oncogene encoding a member of a subfamily of portein-serine/threonine kinases, is amplified in human ovarian carcinomas," *Proc. Nati. Acad. Sci. USA*, Oct. 1992; 89:9267-9271.

Dillon et al., "Akt1 and Akt2 Play Distinct Roles in the Initiation and Metastatic Phases of Mammary Tumor Progression," *Cancer Research*, 2009; 69:5057-5064.

Grant Abstract, Grant No. RO1CA104748, published 2007; 1 page.

Grant Abstract, Grant No. RO1DK048498, published 2007; 1 page.

Grant Abstract, Grant No. RO1DK035608, published 2007; 1 page.

\* cited by examiner

SIRNA INHIBITION OF PI3K P85, P110, AND AKT2 AND METHODS OF USE

CONTINUING APPLICATION DATA

This application is a U.S. National Stage Application of International Application No. PCT/US2007/011917, filed May 18, 2007, published in the English language on Nov. 29, 2007 as International Publication No. WO 2007/136758 A2, which claims the benefit of U.S. Provisional Application Serial No. 60/801,729, filed May 19, 2006, both of which are incorporated by reference herein.

GOVERNMENT FUNDING

The present invention was made with government support under Grant Nos. RO1CA104748, RO1DK48498, PO1DK35608, and T32DK07639, awarded by the National Institutes of Health. The Government may have certain rights in this invention.

BACKGROUND

Phosphatidylinositol 3-kinase (PI3K), a ubiquitous lipid kinase involved in receptor signal transduction by tyrosine kinase receptors, includes a large and complex family that includes 3 classes with multiple subunits and isoforms (Cantley, Science 296:1655-1657 (2002); Carpenter and Cantley, Curr. Opin. Cell Biol., 8:153-8 (1996)). The class I PI3Ks are composed of a Src homology-2 domain-containing an 85 kDa regulatory subunit (p85) and a 110-kDa catalytic subunit (p110), which catalyze the phosphorylation of phosphoinositol 4-phosphate and phosphoinositol 4,5-phosphate at their D3 position (Cantley, Science 296:1655-1657 (2002); Carpenter and Cantley, Curr. Opin. Cell Biol., 8:153-8 (1996)). The PI3K regulatory subunits include p85α and its truncated splice variants p50α and p55α, as well as p85β and p55γ; the catalytic subunits include p110α, p110β, and p110δ (Cantley, Science 296:1655-1657 (2002)). The regulatory subunits p85α, p50α, and p55α are encoded by the pik3r1 gene; p85α is the most abundantly expressed regulatory isoform of PI3K, and p55α and p50α are 2 additional minor alternative splicing isoforms (Ueki et al., Mol. Cell. Biol. 20:8035-8046 (2000)).

The type I enzymes have been extensively studied and were originally identified in association with tyrosine kinases such as growth factor receptors and products of oncogenes (Khaleghpour et al., Carcinogenesis, 25:241-248 (2004)). Most studies regarding the type I PI3Ks have focused on the a form. In particular, class IA PI3Ks are strongly expressed in colonic epithelial carcinoma cell lines (Shao et al., Cancer Res., 64:229-235 (2004)). The gene coding for p110α (pik3cα) is amplified in ovarian and breast tumors (Campbell et al., Cancer Res., 64:7678-7681 (2004)), implicating pik3cα as a potential oncogene in these cancers. An oncogenic mutated form of p85α has also been described (Jimenez et al., EMBO J., 17:743-753 (1998)), expression of this allele associates with endogenous p110 and increases its activity in a constitutive manner, leading to cell transformation. In addition to the regulation of normal cell processes, the promotion of cell survival by the activation of PI3K occurs by the inhibition of proapoptotic signals and the induction of survival signals, which contribute to the malignant transformation and tumor progression (9). In this regard, there is a growing body of evidence to support the notion that the activation of PI3K/Akt is associated with colorectal carcinoma and can convert differentiated human gastric or colonic carcinoma cells to a less differentiated and more malignant phenotype (Semba et al., Clin. Cancer Res., 8:3824-3831 (2002)). The effects of PI3K on tumor growth and progression are thought to be mediated by Akt, a downstream effector of PI3K (Fresno Vara et al., Cancer Treat Rev., 30:193-204 (2004)). The Akt family defines a family of closely related highly conserved cellular homologs of the viral oncoprotein v-akt (Bellacosa et al., Science., 254:274-277 (1991)). In humans, there are 3 members of the Akt gene family, designated Akt1, Akt2, and Akt3, which are located on different chromosomes. The Akt gene products, cytoplasmic serine/threonine (ser/thr)-specific protein kinases, are major downstream targets of numerous receptor tyrosine kinases signaling via PI3K (Fresno Vara et al., Cancer Treat. Rev., 30:193-204 (2004)). Akt is overexpressed in a number of cancers, including colon, pancreatic, ovarian, and some steroid hormone-insensitive breast cancers (Roy et al., Carcinogenesis, 23:201-205 (2002); Asano et al., Oncogene, 23:8571-8580 (2004)). Moreover, it has been reported that Akt phosphorylation in human colon carcinomas correlates with cell proliferation and apoptosis inhibition, as well as with different clinicopathologic parameters such as invasion grade, vessel infiltration, metastasis to lymph nodes, and tumor stage (Khaleghpour et al., Carcinogenesis, 25:241-248 (2004); Itoh et al,. Cancer, 94:3127-3134 (2002)).

Inhibitors of proteins that are involved in PI3K/Akt signaling have been suggested as potential therapeutic agents. These include inhibitors that target both upstream regulators of PI3K/Akt, such as growth factor receptors, PI3K and Akt inhibitors, and downstream effectors, such as the components of the mTOR pathway. The components of the regulatory system for PI3K/Akt that have proved most amenable to therapeutic intervention are the growth-factor-receptor tyrosine kinases, in particular, the epidermal growth factor receptor (EGFR), its close relative ERBB2, and the fungal metabolite wortmannin, a PI3K inhibitor (Wang et al., Clin Cancer Res. 8:1940-1947 (2002); Hortobagyi, Cancer., 88 (suppl 12):3073-3079 (2000)). Disadvantages of wortmannin include its short half-life, solubility in organic solvents, and toxicity, which limits its use in clinical trials (Gunther et al., Food Chem. Toxicol., 27:173-179 (1998)). An alternative approach to the therapeutic targeting of the PI3K/Akt pathway is to specifically inhibit the expression of important pathway proteins by RNA interference (RNAi). RNAi is an evolutionary conserved mechanism that is operative in insects, nematodes, plants, and mammalian cells (Matzke and Birchler, Nat. Rev. Genet., 6:24-35 (2005)). In this process, sequence-specific posttranscriptional silencing is initiated by the introduction into cells of double-stranded annealed sense and antisense RNAs that are homologous to the sequence of the silenced gene (Matzke and Birchler, Nat. Rev. Genet., 6:24-35 (2005)). Small interfering RNAs (siRNAs) can be targeted to tumors, and several recent studies indicate the potential for application of this technique in the therapy for various cancers (Yin et al., J. Exp. Ther., 3:194-204 (2003); Takeshita et al., Proc. Natl. Acad. Sci., USA, 102:12177-12782 (2005)).

SUMMARY OF THE INVENTION

Shortly after the discovery that siRNA duplexes can specifically silence mammalian genes, it was thought that almost any target-complementary siRNA effectively and specifically silences its cognate target gene (Elbashir et al. Genes Dev., 15:188-200 (2001)). In practice, however, different siRNAs often manifest a spectrum of potency, and only a fraction of them are highly effective (Caplen et al., Proc. Natl. Acad. Sci., USA, 89:9742-9747 (2001)). Small positional shifts along the target mRNA were sufficient to alter siRNA function in an apparently unpredictable manner (Caplen et al. Proc. Natl. Acad. Sci. USA, 98:9742-9747 (2001); Paddison et al., Genes Dev., 16:948-958 (2002); Rose et al., Nucl. Acids Res., 33:4140-4156 (2005)). Moreover, siRNAs may nonspecifically target unrelated genes with only partial sequence-complementarity (off-target effects) (Marques et al., Nat. Biotech., 24:559-565 (2006); Qiu et al., Nucl. Acids Res., 33:1834-1847 (2005); Lin et al., Nucl. Acids Res., 33:4527-4535 (2005); Birmingham et al., Nat. Meth., 3:199-204 (2006); Pei and Tuschl, Nat. Meth., 3:670-676 (2006)).

The present invention presents the identification of RNA polynucleotide duplexes that inhibit the expression of certain coding regions, and methods for using the polynucleotides. The present invention provides methods for treating cancer in a subject. The methods include administering to a subject an effective amount of a double stranded polynucleotide. The polynucleotide may be delivered locally, for instance by suppository, or rectal enema, or systemically, for instance intravenously. The cancers treated by the methods include colorectal cancers, breast cancers, and lung cancers. The cancers treated by the methods also include metastases of primary cancers, such as colorectal cancers, breast cancers, and lung cancers. Such metastatic cancers may be present in the liver of the subject. The subject may have the cancer or be at risk of developing the cancer.

The administered polynucleotide may be a vector, such as a vector which encodes one or both strands of an siRNA. The polynucleotide may include one or more ribonucleotides or be made up entirely of ribonucleotides, and may include one or more modified nucleotides. The double stranded polynucleotide may include a sense strand that is 19 to 29 nucleotides in length.

In some aspects, the polynucleotide includes a nucleotide sequence that is substantially identical, preferably identical, to consecutive nucleotides of a target mRNA encoded by a pik3ca coding region. An example of such a target mRNA is one that encodes a p110α polypeptide (SEQ ID NO:7). Examples of polynucleotides useful to inhibit expression of a p110α polypeptide include SEQ ID NO:13, SEQ ID NO:14, SEQ ID NO:15, and SEQ ID NO:16.

In other aspects, the polynucleotide includes a nucleotide sequence that is substantially identical, preferably identical, to consecutive nucleotides of a target mRNA encoded by a pik3r1 coding region. An example of such a target mRNA is one that encodes a p85α polypeptide (SEQ ID NO:2). Examples of polynucleotides useful to inhibit expression of a p85α polypeptide include SEQ ID NO:9, SEQ ID NO:10, SEQ ID NO:11, and SEQ ID NO:12.

In yet another aspect, the polynucleotide includes a nucleotide sequence that is substantially identical, preferably identical, to consecutive nucleotides of a target mRNA encoded by an akt2 coding region. An example of such a target mRNA is one that encodes an Akt2 polypeptide (SEQ ID NO:18). Examples of polynucleotides useful to inhibit expression of an Akt2 polypeptide include SEQ ID NO:20.

The terms "comprises" and variations thereof do not have a limiting meaning where these terms appear in the description and claims. Unless otherwise specified, "a," "an," "the," and "at least one" are used interchangeably and mean one or more than one.

The above summary of the present invention is not intended to describe each disclosed embodiment or every implementation of the present invention. The description that follows more particularly exemplifies illustrative embodiments. In several places throughout the application, guidance is provided through lists of examples, which examples can be used in various combinations. In each instance, the recited list serves only as a representative group and should not be interpreted as an exclusive list.

Figure 1:
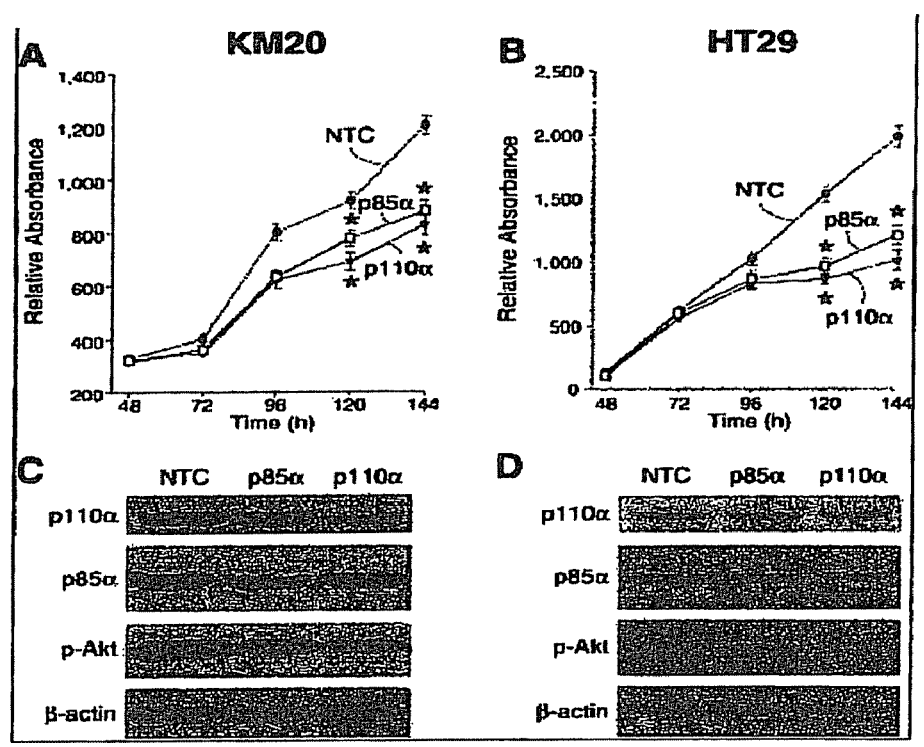
FIG. 1. siRNA directed against p85α or p110α inhibits proliferation. The effect of siRNA directed to PI3K components on the viability of KM20 (A) or HT29 (B) cells was assessed. Cell viability was measured as described in Example 1. Points represent means of triplicate determinations±SD. *$P<0.05$ for p85α, p110α siRNA compared with nontargeting control (NTC) siRNA. KM20 (C) or HT29 (D) cells transfected with p85α, p110α, or NTC. siRNA sequences were lysed and Western blots performed using anti-Akt, phospho (Ser473), anti-p85α, and anti-p110α; β-actin was used as a loading control (bottom row).

Western blot analysis of the cells used for intrasplenic inoculation before (0 h) or after (2 h) surgical procedure.

DETAILED DESCRIPTION OF ILLUSTRATIVE EMBODIMENTS

The present invention includes polynucleotides and the uses thereof. As used herein, the term "polynucleotide" refers to a polymeric form of nucleotides of any length, either ribonucleotides, deoxynucleotides, or a combination thereof, and includes both single-stranded molecules and double-stranded duplexes. A polynucleotide can be obtained directly from a natural source, or can be prepared with the aid of recombinant, enzymatic, or chemical techniques. Preferably, a polynucleotide of the present invention is isolated. An "isolated" polynucleotide is one that has been removed from its natural environment. Polynucleotides that are produced by recombinant, enzymatic, or chemical techniques are considered to be isolated and purified by definition, since they were never present in a natural environment. As used herein, "coding region" and "coding sequence" are used interchangeably and refer to a nucleotide sequence that encodes an mRNA or an unprocessed preRNA (i.e., an RNA molecule that includes both exons and introns) that is processed to produce an mRNA. As used herein, a "target coding region" and "target coding sequence" refer to a specific coding region whose expression is inhibited by a polynucleotide of the present invention. As used herein, a "target mRNA" is an mRNA encoded by a target coding region. Unless noted otherwise, a target coding region can result in multiple mRNAs distinguished by the use of different combinations of exons. Such related mRNAs are referred to as splice variants of a coding region.

In some aspects of the present invention, polynucleotides include double stranded RNA (dsRNA) polynucleotides. The sequence of a polynucleotide of the present invention includes one strand, referred to herein as the sense strand, of between 19 and 29 nucleotides, for instance, 19, 20, 21, 22, 23, 24, 25, 26, 27, 28, or 29 nucleotides. The sense strand is substantially identical, preferably, identical, to a target mRNA. As used herein, the term "identical" means the nucleotide sequence of the sense strand has the same nucleotide sequence as a portion of the target mRNA. As used herein, the term "substantially identical" means the sequence of the sense strand differs from the sequence of a target mRNA at 1 or 2 nucleotides, and the remaining nucleotides are identical to the sequence of the mRNA. These 1 or 2 nucleotides of the sense strand are referred to as non-complementary nucleotides. When a polynucleotide of the present invention includes a sense strand that is substantially identical to a target mRNA, the 1 or 2 non-complementary nucleotides can be located anywhere in the polynucleotide (Birmingham et al., Nat. Meth., 3:199-204 (2006); Pei and Tuschl, Nat. Meth., 3:670-676 (2006)). The other strand of a dsRNA polynucleotide, referred to herein as the antisense strand, includes nucleotides that are complementary to the sense strand. The antisense strand may be between 19 and 29 nucleotides, for instance, 19, 20, 21, 22, 23, 24, 25, 26, 27, 28, or 29 nucleotides. In some aspects, the sense strand and the antisense strand of a double stranded polynucleotide, preferably, a dsRNA, have different lengths (Marques et al., Nat. Biotech., 24:559-565 (2006)). The term "complementary" refers to the ability of two single stranded polynucleotides to base pair with each other, where an adenine on one polynucleotide will base pair to a thymine or uracil on a second polynucleotide and a cytosine on one polynucleotide will base pair to a guanine on a second polynucleotide. The polynucleotides of the present invention also include the double stranded DNA polynucleotides that correspond to the dsRNA polynucleotides of the present invention. Also included in the present invention are the single stranded RNA polynucleotide and single stranded DNA (dsDNA) polynucleotides corresponding to the sense strands and antisense strands disclosed herein. It should be understood that the sequences disclosed herein as DNA sequences can be converted from a DNA sequence to an RNA sequence to replacing each thymidine nucleotide with a uracil nucleotide.

A polynucleotide of the present invention may include overhangs on one or both strands of a double stranded polynucleotide. An overhang is one or more nucleotides present in one strand of a double stranded polynucleotide that are unpaired, i.e., they do not have a corresponding complementary nucleotide in the other strand of the double stranded polynucleotide. An overhang may be at the 3' end of a sense strand, an antisense strand, or both sense and antisense strands. An overhang is typically 1, 2, or 3 nucleotides in length. A preferred overhang is at the 3' terminus and has the sequence thymine-thymine (or uracil-uracil if it is an RNA). Without intending to be limiting, such an overhang can be used to increase the stability of a dsRNA. If an overhang is present, it is preferably not considered a non-complementary nucleotide when determining whether a sense strand is identical or substantially identical to a target mRNA.

The sense and antisense strands of a dsRNA polynucleotide of the present invention may also be covalently attached, for instance, by a spacer made up of nucleotides. Such a polynucleotide is often referred to in the art as a short hairpin RNA (shRNA). Upon base pairing of the sense and antisense strands, the spacer region forms a loop. The number of nucleotides making up the loop can vary, and loops between 3 and 23 nucleotides have been reported (Sui et al., Proc. Nat'l. Acad. Sci. USA, 99:5515-5520 (2002), and Jacque et al., Nature, 418:435-438 (2002)).

Polynucleotides of the present invention are biologically active. A biologically active polynucleotide causes the post-transcriptional inhibition of expression, also referred to as silencing, of a target coding region. Without intending to be limited by theory, after introduction into a cell a polynucleotide of the present invention will hybridize with a target mRNA and signal cellular endonucleases to cleave the target mRNA. The result is the inhibition of expression of the polypeptide encoded by the mRNA. Whether the expression of a target coding region is inhibited can be determined by, for instance, measuring a decrease in the amount of the target mRNA in the cell, measuring a decrease in the amount of polypeptide encoded by the mRNA, or by measuring a decrease in the activity of the polypeptide encoded by the mRNA. As used herein, the term "polypeptide" refers broadly to a polymer of two or more amino acids joined together by peptide bonds. The term "polypeptide" also includes molecules which contain more than one polypeptide joined by a disulfide bond, or complexes of polypeptides that are joined together, covalently or noncovalently, as multimers (e.g., dimers, tetramers). Thus, the terms peptide, oligopeptide, and protein are all included within the definition of polypeptide and these terms are used interchangeably.

Polynucleotides of the present invention may be modified. Such modifications can be useful to increase stability of the polynucleotide in certain environments. Modifications can include a nucleic acid sugar, base, or backbone, or any combination thereof. The modifications can be synthetic, naturally occurring, or non-naturally occurring. A polynucleotide of the present invention can include modifications at one or more of the nucleic acids present in the polynucleotide.

Examples of backbone modifications include, but are not limited to, phosphonoacetates, thiophosphonoacetates, phosphorothioates, phosphorodithioates, phosphoramidates, methyl phosphonates, chiral-methyl phosphonates, 2-O-methyl ribonucleotides, and peptide-nucleic acids. Examples of nucleic acid base modifications include, but are not limited to, inosine, purine, pyridin-4-one, pyridin-2-one, phenyl, pseudouracil, 2,4,6-trimethoxy benzene, 3-methyl uracil, dihydrouridine, naphthyl, aminophenyl, 5-alkylcytidines (e.g., 5-methylcytidine), 5-alkyluridines (e.g., ribothymidine), 5-halouridine (e.g., 5-bromouridine) or 6-azapyrimidines or 6-alkylpyrimidines (e.g. 6-methyluridine), or propyne modifications. Examples of nucleic acid sugar modifications include, but are not limited to, 2'-sugar modification, e.g., 2'-O-methyl nucleotides, 2'-deoxy-2'-fluoro nucleotides, 2'-deoxy-2'-fluoroarabino, 2'-O-methoxyethyl nucleotides, 2'-O-trifluoromethyl nucleotides, 2'-O-ethyl-trifluoromethoxy nucleotides, 2'-O-difluoromethoxy-ethoxy nucleotides, or 2'-deoxy nucleotides. Polynucleotides can be obtained commercially synthesized to include such modifications (for instance, Dharmacon Inc., Lafayette, Colo.).

In one aspect, the present invention includes polynucleotides that inhibit expression of a polypeptide encoded by a pik3r1 coding region. As used herein a pik3r1 coding region refers to the genomic nucleotide sequence disclosed at Genbank accession number NM_181523 (SEQ ID NO:1). Several splice variants of the pik3r1 coding region are expressed and encode polypeptides including a p85α polypeptide, a p55α polypeptide, and a p50α polypeptide. An example of a target mRNA encoding a p85 α polypeptide is the sequence available at Genbank accession number NM_181523 (SEQ ID NO:3). A preferred target mRNA includes a sequence that is present in all three splice variants. Polynucleotides of the present invention that will act to inhibit expression of a p85α polypeptide, a p55α polypeptide, and a p50α polypeptide include polynucleotides with a sense strand that is substantially identical or identical to a region of SEQ ID NO:1 that includes, for instance, nucleotides 1205-1230 or 2041-2059 of SEQ ID NO:1. Examples of such polynucleotides that will act to inhibit expression of a polypeptide encoded by a pik3r1 coding region include GGAAAUAUGGCUUCUCUGAUU (SEQ ID NO:9), GAAAGACGAGAGACCAAUAUU (SEQ ID NO:10), GUAAAGCAUUGUGUCAUAAUU (SEQ ID NO:11), and UGGCUUCUCUGACCCAUUAUU (SEQ ID NO:12). SEQ ID NO:9, SEQ ID NO:11 AND SEQ ID NO:12 inhibit expression of a p85α polypeptide, a p55α polypeptide, and a p50α polypeptide.

As used herein a "p85α polypeptide" refers to a polypeptide having a molecular weight of 85 kilodaltons (kDa) as determined by sodium dodecyl sulfate (SDS) polyacrylamide gel electrophoresis, and bound by an antibody that specifically binds to a human p85α polypeptide, such as the polypeptide disclosed at Genbank accession number NM_181523 (SEQ ID NO:2). Such antibodies are commercially obtainable from, for instance, Upstate USA, Inc. (Chicago, Ill.). As used herein, an antibody that can specifically bind a polypeptide is an antibody that interacts only with the epitope of the antigen that induced the synthesis of the antibody, or interacts with a structurally related epitope. An antibody that specifically binds to an epitope will, under the appropriate conditions, interact with the epitope even in the presence of a diversity of potential binding targets. With respect to the activity of a p85α polypeptide the docking of PI3K in the vicinity of the plasma membrane through p85α recognition of the receptor phosphorylated YXXM activates the PI3K pathway (Cantley, Science 296:1655-1657 (2002); Rush et al. Nat. Biotech., 23:94-101 (2005); Okkenhaug Vanhaesebroeck, Sci. STKE 2001 (65):PE1 (Jan. 16, 2001)). Methods for measuring the activity of a p85α polypeptide are routine and known in the art.

As used herein a "p55α polypeptide" refers to a polypeptide having a molecular weight of 55 kDa as determined by SDS polyacrylamide gel electrophoresis, and bound by an antibody that specifically binds to a human p55α polypeptide, such as the polypeptide disclosed at Genbank accession number NM_181504 (SEQ ID NO:4).

As used herein a "p50α polypeptide" refers to a polypeptide having a molecular weight of 50 kDa as determined by SDS polyacrylamide gel electrophoresis, and bound by an antibody that specifically binds to a human p50α polypeptide, such as the polypeptide disclosed at Genbank accession number NM_181524 (SEQ ID NO:4).

The present invention also includes polynucleotides that inhibit production of a polypeptide encoded by a pik3ca coding region. As used herein a pik3ca coding region refers to the genomic nucleotide sequence disclosed at GenBank accession number NM_006218 (SEQ ID NO:6). One polypeptide encoded by a pik3ca coding region is a p110α polypeptide. As used herein a "p110α polypeptide" refers to a polypeptide having a molecular weight of 110 kDa as determined by SDS polyacrylamide gel electrophoresis, and bound by an antibody that specifically binds to a human p110α polypeptide, such as the polypeptide disclosed at Genbank accession number NM_006218 (SEQ ID NO:7). Such antibodies are commercially obtainable from, for instance, Cell Signaling Technology, Inc. (Danvers, Mass.). A p110α polypeptide is an intermediate in IGF-1, insulin and leptin signaling. An example of a target mRNA encoding a p110α polypeptide is the sequence available at Genbank accession number NM_006218 (SEQ ID NO:8). Examples of polynucleotides of the present invention that will act to inhibit production of a p110α polypeptide include polynucleotides having a sense strand that includes AUGUUUACUACCAAAUGGA (SEQ ID NO:13), AACUAGAAGUAUGUUGCUA (SEQ ID NO:14), AAUGGCUUUGAAUCUUUGG (SEQ ID NO:15), and CUGAAGAAAGCAUUGACUA (SEQ ID NO:16).

The present invention also includes polynucleotides that inhibit expression of a polypeptide encoded by an akt2 coding region. As used herein an akt2 coding region refers to the genomic nucleotide sequence disclosed at Genbank accession number NM_001626 (SEQ ID NO:17). One polypeptide encoded by an akt2 coding region is an Akt2 polypeptide. As used herein an "Akt2 polypeptide" refers to a polypeptide having a molecular weight of 60 kDa as determined by SDS polyacrylamide gel electrophoresis, and bound by an antibody that specifically binds to a human Akt2 polypeptide, such as the polypeptide disclosed at GenBank accession number NP_001617 (SEQ ID NO:18). Such antibodies are commercially obtainable from, for instance, Cell Signaling Technology, Inc. (Danvers, Mass.). An Akt2 polypeptide has kinase activity and plays role in insulin signaling (Kim et al., Diabetes 49:847-856 (2000)). An example of a target mRNA encoding an Akt2 polypeptide is the sequence available at Genbank accession number NM_001626 (SEQ ID NO:19). Polynucleotides of the present invention that will act to inhibit expression of an Akt2 polypeptide include polynucleotides with a sense strand that is substantially identical or identical to nucleotides of a target mRNA. Examples of such polynucleotides that will act to inhibit expression of a polypeptide encoded by an akt2 coding region include GUACUUCGAUGAUGAAUUU (SEQ ID NO:20).

A polynucleotide of the present invention can be present in a vector. A vector is a replicating polynucleotide, such as a plasmid, phage, or cosmid, to which another polynucleotide may be attached so as to bring about the replication of the attached polynucleotide. Construction of vectors containing a polynucleotide of the invention employs standard ligation techniques known in the art. See, e.g., Sambrook et al, *Molecular Cloning: A Laboratory Manual.*, Cold Spring Harbor Laboratory Press (1989). A vector can provide for further cloning (amplification of the polynucleotide), i.e., a cloning vector, or for expression of the polynucleotide, i.e., an expression vector. The term vector includes, but is not limited to, plasmid vectors, viral vectors, cosmid vectors, or artificial chromosome vectors. Examples of viral vectors include, for instance, adenoviral vectors, adeno-associated viral vectors, lentiviral vectors, retroviral vectors, and herpes virus vectors. A vector may result in integration into a cell's genomic DNA. Typically, a vector is capable of replication in a bacterial host, for instance *E. coli*. Preferably the vector is a plasmid. A polynucleotide of the present invention can be present in a vector as two separate complementary polynucleotides, each of which can be expressed to yield a sense and an antisense strand of the dsRNA, or as a single polynucleotide containing a sense strand, a loop region, and an antisense strand, which can be expressed to yield an RNA polynucleotide having a sense and an antisense strand of the dsRNA.

Selection of a vector depends upon a variety of desired characteristics in the resulting construct, such as a selection marker, vector replication rate, and the like. Suitable host cells for cloning or expressing the vectors herein are prokaryotic or eukaryotic cells. Suitable eukaryotic cells include mammalian cells, such as murine cells and human cells. Suitable prokaryotic cells include eubacteria, such as gram-negative organisms, for example, *E. coli*.

An expression vector optionally includes regulatory sequences operably linked to the polynucleotide of the present invention. Typically, the promoter results in the production of an RNA polynucleotide. Examples of such promoters include, but are not limited to, those that cause binding of an RNA polymerase III complex to initiate transcription of an operably linked polynucleotide of the present invention. Examples of such promoters include U6 and H1 promoters. Vectors may also include inducible or regulatable promoters for expression of a polynucleotide of the present invention in a particular tissue or intracellular environment. The polynucleotide of the present invention also typically includes a transcription terminator. Suitable transcription terminators are known in the art and include, for instance, a stretch of 5 consecutive thymidine nucleotides.

Polynucleotides of the present invention can be produced in vitro or in vivo. For instance, methods for in vitro synthesis include, but are not limited to, chemical synthesis with a conventional DNA/RNA synthesizer. Commercial suppliers of synthetic polynucleotides and reagents for such synthesis are well known. Methods for in vitro synthesis also include, for instance, in vitro transcription using a circular or linear expression vector in a cell free system. Expression vectors can also be used to produce a polynucleotide of the present invention in a cell, and the polynucleotide then isolated from the cell.

The present invention is also directed to compositions including one or more polynucleotides of the present invention. Such compositions typically include a pharmaceutically acceptable carrier. As used herein "pharmaceutically acceptable carrier" includes saline, solvents, dispersion media, coatings, antibacterial and antifungal agents, isotonic and absorption delaying agents, and the like, compatible with pharmaceutical administration. Additional active compounds can also be incorporated into the compositions.

A composition may be prepared by methods well known in the art of pharmacy. In general, a composition can be formulated to be compatible with its intended route of administration. Examples of routes of administration include perfusion and parenteral, e.g., intravenous, intradermal, subcutaneous, oral (e.g., inhalation), transdermal (topical), transmucosal, and rectal administration. Solutions or suspensions can include the following components: a sterile diluent such as water for administration, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates; electrolytes, such as sodium ion, chloride ion, potassium ion, calcium ion, and magnesium ion, and agents for the adjustment of tonicity such as sodium chloride or dextrose. pH can be adjusted with acids or bases, such as hydrochloric acid or sodium hydroxide. A composition can be enclosed in, ampoules, disposable syringes or multiple dose vials made of glass or plastic.

Compositions can include sterile aqueous solutions or dispersions and sterile powders for the extemporaneous preparation of sterile solutions or dispersions. For intravenous administration, suitable carriers include physiological saline, bacteriostatic water, Cremophor EL™ (BASF, Parsippany, N.J.) or phosphate buffered saline. A composition is typically sterile and, when suitable for injectable use, should be fluid to the extent that easy syringability exists. It should be stable under the conditions of manufacture and storage and preserved against the contaminating action of microorganisms such as bacteria and fungi. The carrier can be a solvent or dispersion medium containing, for example, water, ethanol, polyol (for example, glycerol, propylene glycol, and liquid polyetheylene glycol, and the like), and suitable mixtures thereof. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as mannitol, sorbitol, sodium chloride in the composition. Prolonged absorption of the injectable compositions can be brought about by including in the composition an agent which delays absorption, for example, aluminum monostearate and gelatin.

Sterile solutions can be prepared by incorporating the active compound (e.g., a polynucleotide of the present invention) in the required amount in an appropriate solvent with one or a combination of ingredients enumerated above, as required, followed by filtered sterilization. Generally, dispersions are prepared by incorporating the active compound into a sterile vehicle, which contains a dispersion medium and the required other ingredients from those enumerated above. In the case of sterile powders for the preparation of sterile injectable solutions, the preferred methods of preparation are vacuum drying and freeze-drying which yields a powder of the active ingredient plus any additional desired ingredient from a previously sterile-filtered solution thereof.

Oral compositions generally include an inert diluent or an edible carrier. For the purpose of oral therapeutic administration, the active compound can be incorporated with excipients and used in the form of tablets, troches, or capsules, e.g., gelatin capsules. Oral compositions can also be prepared using a fluid carrier. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

For administration by inhalation, the active compounds are delivered in the form of an aerosol spray from a pressured container or dispenser which contains a suitable propellant, e.g., a gas such as carbon dioxide, or a nebulizer.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art. An example of transdermal administration includes iontophoretic delivery to the dermis or to other relevant tissues.

The active compounds can also be prepared in the form of suppositories (e.g., with conventional suppository bases such as cocoa butter and other glycerides) or retention enemas for rectal delivery.

The active compounds can also be administered by any method suitable for administration of polynucleotide agents, e.g., using gene guns, bio injectors, and skin patches as well as needle-free methods such as the micro-particle DNA vaccine technology disclosed by Johnston et al. (U.S. Pat. No. 6,194,389). Additionally, intranasal delivery is possible, as described in, for instance, Hamajima et al. Clin. Immunol. Immunopathol., 88, 205-210 (1998). Liposomes and microencapsulation can also be used.

The active compounds may be prepared with carriers that will protect the compound against rapid elimination from the body, such as a controlled release formulation, including implants. Biodegradable, biocompatible polymers can be used, such as ethylene vinyl acetate, polyanhydrides, polyglycolic acid, collagen, polyorthoesters, and polylactic acid. Such formulations can be prepared using standard techniques. The materials can also be obtained commercially. Liposomal suspensions can also be used as pharmaceutically acceptable carriers. These can be prepared according to methods known to those skilled in the art.

Toxicity and therapeutic efficacy of such active compounds can be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio $LD_{50}/ED_{50}$. Compounds which exhibit high therapeutic indices are preferred.

The data obtained from cell culture assays and animal studies can be used in formulating a range of dosage for use in humans. The dosage of such compounds lies preferably within a range of circulating concentrations that include the $ED_{50}$ with little or no toxicity. The dosage may vary within this range depending upon the dosage form employed and the route of administration utilized. For a compound used in the methods of the invention, the therapeutically effective dose can be estimated initially from cell culture assays. A dose may be formulated in animal models to achieve a circulating plasma concentration range that includes the $IC_{50}$ (i.e., the concentration of the test compound which achieves a half-maximal inhibition of symptoms) as determined in cell culture. Such information can be used to more accurately determine useful doses in humans.

The compositions can be administered one or more times per day to one or more times per week, including once every other day. The skilled artisan will appreciate that certain factors may influence the dosage and timing required to effectively treat a subject, including but not limited to the severity of the disease or disorder, previous treatments, the general health and/or age of the subject, and other diseases present. Moreover, treatment of a subject with an effective amount of a polypeptide can include a single treatment or can include a series of treatments.

The polynucleotides of the present invention can be designed using methods that are routine and known in the art. For instance, polynucleotides that inhibit the expression of one of the polypeptides described herein may be identified by the use of cell lines including, but not limited to, HT29 and KM20. A candidate polynucleotide is the polynucleotide that is being tested to determine if it decreases expression of one of the polypeptides described herein. The candidate polynucleotide can be identical to nucleotides located in the region encoding the polypeptide, or located in the 5' or 3' untranslated regions of the mRNA. Other methods are known in the art and used routinely for designing and selecting candidate polynucleotides. Candidate polynucleotides are typically screened using publicly available algorithms (e.g., BLAST) to compare the candidate polynucleotide sequences with coding sequences. Those that are likely to form a duplex with an mRNA expressed by a non-target coding region are typically eliminated from further consideration. The remaining candidate polynucleotides may then be tested to determine if they inhibit expression of one of the polypeptides described herein.

In general, candidate polynucleotides are individually tested by introducing a candidate polynucleotide into a cell that expresses the appropriate polypeptide. The candidate polynucleotides may be prepared in vitro and then introduced into a cell. Methods for in vitro synthesis include, for instance, chemical synthesis with a conventional DNA/RNA synthesizer. Commercial suppliers of synthetic polynucleotides and reagents for such synthesis are well known. Methods for in vitro synthesis also include, for instance, in vitro transcription using a circular or linear vector in a cell free system.

The candidate polynucleotides may also be prepared by introducing into a cell a construct that encodes the candidate polynucleotide. Such constructs are known in the art and include, for example, a vector encoding and expressing a sense strand and an antisense strand of a candidate polynucleotide, and RNA expression vectors that include the sequence encoding the sense strand and an antisense strand of a candidate polynucleotide flanked by operably linked regulatory sequences, such as an RNA polymerase III promoter and an RNA polymerase III terminator, that result in the production of an RNA polynucleotide.

A cell that can be used to evaluate a candidate polynucleotide may be a cell that expresses the appropriate polypeptide. A cell can be ex vivo or in vivo. As used herein, the term "ex vivo" refers to a cell that has been removed from the body of a subject. Ex vivo cells include, for instance, primary cells (e.g., cells that have recently been removed from a subject and are capable of limited growth in tissue culture medium), and cultured cells (e.g., cells that are capable of extended culture in tissue culture medium). As used herein, the term "in vivo" refers to a cell that is within the body of a subject. Whether a cell expresses one of the polypeptides can be determined using methods that are routine and known in the art including, for instance, Western immunoblot, ELISA, immunoprecipitation, or immunohistochemistry. Western immunoblot and immunoprecipitation are generally used with ex vivo cells, and immunohistochemistry is generally used with in vivo cells. Examples of readily available cells expressing a polypeptide encoded by a pik3r1 coding region include cultured cells such as HT29 (ATCC number HTB 38), and primary cells such as epithelial cells. Examples of cells expressing a polypeptide encoded by a pik3ca coding region include cultured cells such as HT29 (ATCC number HTB 38), and primary cells such as epithelial cells. Other cells can also be modified to express one of the polypeptides by introducing into a cell a vector having a polynucleotide encoding the polypeptide.

Candidate polynucleotides may also be tested in animal models. The study of various cancers in animal models (for instance, mice) is a commonly accepted practice for the study of cancers. For instance, the nude mouse model, where human tumor cells are injected into the animal, is commonly accepted as a general model useful for the study of a wide variety of cancers (see Example 1). Experimental liver metastasis model is also widely used for studying the relevant host organ factors that regulate the pathogenesis of colorectal cancer metastasis (Morikawa et al., Cancer Res., 48:1943-1948 (1988); Morikawa et al., Cancer Res., 48:6863-6871 (1988)). Candidate polynucleotides can be used in these and other animal models to determine if a candidate polynucleotide decreases one or more symptoms associated with the disease.

Methods for introducing a candidate polynucleotide, including a vector encoding a candidate polynucleotide, are known in the art and routine. When the cells are ex vivo, such methods include, for instance, transfection with lipid or amine based reagents such as cationic liposomes or polymeric DNA-binding cations (such as poly-L-lysine and polyethyleneimine). Alternatively, electroporation or viral transfection can be used to introduce a candidate polynucleotide, or a vector encoding a candidate polynucleotide. When the cells are in vivo, such methods include, but are not limited to, intravenous administration.

When evaluating whether a candidate polynucleotide functions to inhibit expression of one of the polypeptides described herein, the amount of target mRNA in a cell containing a candidate polynucleotide can be measured and compared to the same type of cell that does not contain the candidate polynucleotide. Methods for measuring mRNA levels in a cell are known in the art and routine. Such methods include quantitative reverse-transcriptase polymerase chain reaction (RT-PCR). Primers and specific conditions for amplification of an mRNA vary depending upon the mRNA, and can be readily determined by the skilled person. Other methods include, for instance, Northern blotting, and array analysis.

Other methods for evaluating whether a candidate polynucleotide functions to inhibit expression of one of the polypeptides described herein include monitoring the polypeptide. For instance, assays can be used to measure a decrease in the amount of polypeptide encoded by the mRNA, or to measure a decrease in the activity of the polypeptide encoded by the mRNA. Methods for measuring a decrease in the amount of a polypeptide include assaying for the polypeptide present in cells containing a candidate polynucleotide and comparing to the same type of cell that does not contain the candidate polynucleotide. For instance, antibody to one of the polypeptides described herein can be used in Western immunoblot, immunoprecipitation, or immunohistochemistry.

Methods for measuring a decrease in the activity of one of the polypeptides, e.g., p85α or p110α, vary depending upon the polypeptide. In general, methods for measuring a decrease in the activity of a polypeptide include assaying the appropriate activity present in a cell containing a candidate polynucleotide and comparing to the same type of cell that does not contain the candidate polynucleotide. Methods for measuring the activity of a p85α polypeptide and a p110α polypeptide are known in the art.

A candidate polynucleotide that is able to decrease the expression of a polypeptide encoded by a pik3r1 coding region, a polypeptide encoded by a pik3ca coding region, or a target mRNA by at least 50%, at least 60%, at least 70%, at least 80%, or at least 90%, is considered to be a polynucleotide of the present invention.

The present invention is further directed to methods of using the polynucleotides described herein. Such methods include treating certain diseases in a subject. The subject is a mammal, including members of the family Muridae (a murine animal such as rat or mouse) and human, preferably a human. As used herein, the term "disease" refers to any deviation from or interruption of the normal structure or function of a part, organ, or system, or combination thereof, of a subject that is manifested by a characteristic symptom or set of symptoms. As used herein, the term "symptom" refers to objective evidence of a disease present in a subject. Symptoms associated with diseases referred to herein and the evaluation of such symptoms are routine and known in the art. Diseases include colorectal cancers, lung cancers, and breast cancers. Such cancers are typically primary cancers, and can include cancerous cells that are not metastatic, and cancerous cells that are metastatic. Examples of such cancers are colon adenocarcinomas and rectal adenocarcinomas. Other diseases can include cancers resulting from metastasis of a cancer, such as metastasis of a primary cancer. The primary cancer that acts as the source of cancer cells for the metastatic cancer can be, for instance, a colorectal cancer (e.g., colon adenocarcinoma), lung cancer, or breast cancer. The metastatic cancer can be located in, for instance, the liver, lymph nodes draining the tissue containing the primary cancer, bone, lungs, and peritoneal carcinomatosis. Typically, whether a subject has a disease, and whether a subject is responding to treatment, may be determined by evaluation of symptoms associated with the disease.

Treatment of a disease can be prophylactic or, alternatively, can be initiated after the development of a disease. Treatment that is prophylactic, for instance, initiated before a subject manifests symptoms of a disease, is referred to herein as treatment of a subject that is "at risk" of developing a disease. An example of a subject that is at risk of developing a disease is a person having a risk factor, such as Familial adenomatous polyposis (FAP), Hereditary nonpolyposis colorectal cancer (HNPCC), Long-standing ulcerative colitis or Crohn's disease. Treatment can be performed before, during, or after the occurrence of the diseases described herein. Treatment initiated after the development of a disease may result in decreasing the severity of the symptoms of the disease, or completely removing the symptoms.

In some aspects, the methods typically include introducing into a cell a composition including an effective amount of one or more polynucleotides of the present invention. As used herein, an "effective amount" is an amount effective to inhibit expression of a polypeptide in a cell, decrease symptoms associated with a disease, or the combination thereof. The polynucleotide may be introduced into a cell as a dsRNA polynucleotide, or as a vector including a DNA polynucleotide that encodes and will express the RNA polynucleotide. More than one type of polynucleotide can be administered. For instance, two or more polynucleotides that are designed to silence the same mRNA can be combined and used in the methods herein. Alternatively, two or more polynucleotides can be used together where the polynucleotides are each designed to silence different mRNAs. Whether a polynucleotide is expected to function in the methods of the present invention can be evaluated using ex vivo models and animal models. Such models are known in the art and are generally accepted as representative of disease in humans and useful for evaluation of methods of treating humans.

The cell may be ex vivo or in vivo. When the cell is ex vivo, the presence of a polypeptide in the cell can be compared with the same type of cell that does not contain the polynucleotide of the invention. Such a cell that does not contain the polynucloetide is referred to as a control cell. A decrease in, for instance, the target mRNA or the amount of polypeptide encoded by the target mRNA in the cell containing a polynucleotide of the present invention indicates the expression of the polypeptide has been inhibited. When the cell is in vivo, it is preferably present in a mammalian subject, preferably, a human.

The methods of the present invention can include administering to a subject having a disease or at risk of developing a disease a composition including an effective amount of a polynucleotide of the present invention, wherein expression of a polypeptide in a cell is decreased, a symptom associated with the disease is decreased, or a combination thereof. Preferred methods for administering one or more of the polynucleotides of the present invention include administration during surgery, for instance surgery to resect a diseased part, organ, system, or combination thereof, of a subject. A diseased part, organ, or system can include, for instance, tumor cells, or biological materials that can accumulate as a result of a disease such as colon cancer. For instance, after removal of cancer cells the surrounding area can be perfused with a solution containing one or more of the polynucleotides of the present invention, or an implant containing one or more of the polynucleotides of the present invention can be placed near the area of resection. The polynucleotides may also be administered by other methods known in the art including, for instance, intravenous administration, rectal administration, continuous or intermittent intra-arterial administration.

The polynucleotides of the present invention can also be administered to a subject in combination with other therapeutic compounds to increase the overall therapeutic effect. Therapeutic compounds useful for the treatment of the diseases described herein are known and used routinely. Examples of useful therapeutic compounds include, for instance, chemotherapeutic drugs such as apoptosis-inducing agents (e.g., TNF-related apoptosis inducing ligand), NF-kB inhibitors, growth factor inhibitors, cell proliferation inhibitors and inhibitors of MDR gene expression.

The present invention also provides a kit for practicing the methods described herein. The kit includes one or more of the polynucleotides of the present invention in a suitable packaging material in an amount sufficient for at least one administration. Optionally, other reagents such as buffers and solutions needed to practice the invention are also included. Instructions for use of the packaged polynucleotide(s) are also typically included.

As used herein, the phrase "packaging material" refers to one or more physical structures used to house the contents of the kit. The packaging material is constructed by well known methods, preferably to provide a sterile, contaminant-free environment. The packaging material has a label which indicates that the polynucleotide(s) can be used for the methods described herein. In addition, the packaging material contains instructions indicating how the materials within the kit are employed to practice the methods. As used herein, the term "package" refers to a solid matrix or material such as glass, plastic, paper, foil, and the like, capable of holding within fixed limits the polynucleotide(s). Thus, for example, a package can be a glass vial used to contain appropriate quantities of the polynucleotide(s). "Instructions for use" typically include a tangible expression describing the conditions for use of the polynucleotide(s).

The present invention is illustrated by the following examples. It is to be understood that the particular examples, materials, amounts, and procedures are to be interpreted broadly in accordance with the scope and spirit of the invention as set forth herein.

EXAMPLE 1

Materials and Methods

Cell Lines, Reagents, and Antibodies. The human colon cancer cell line HT29 was purchased from American Type Culture Collection (Manassas, Va.) and stably transfected with the pEGFPN1 vector (CLONTECH Laboratories, Inc., Mountain View, Calif.). The human colon cancer cell line KM20 (derived from a Dukes' D colon cancer) was obtained from Dr Isaiah Fidler (M. D. Anderson Cancer Center, Houston, Tex.). HT29 cells were grown in McCoy's 5A medium supplemented with 10% fetal bovine serum. KM20 cells were grown in minimum Eagle medium supplemented with 10% fetal bovine serum, 1% sodium pyruvate and 1% nonessential amino acids, 2% MEM essential vitamin, and cultured at 37° C. under an atmosphere containing 5% $CO_2$. Tissue culture media and reagents were obtained from Life Technologies, Inc. (Grand Island, N.Y.). SiSTABLE in vivo SMARTpool siRNA and regular SMARTpool reagents for p85α, p110α, and nontargeting control (NTC) siRNA duplexes were designed and synthesized by Customer SMARTpool siRNA Design from Dharmacon (Lafayette, Colo.). siSTABLE in vivo duplex is chemically modified to extend siRNA stability in vivo compared with unmodified siRNA. siRNAs for silencing expression of p110α include AUGUUUACUAC-CAAAUGGA (SEQ ID NO:13), AACUAGAAGUAUG-UUGCUA (SEQ ID NO:14), AAUGGCUUUGAAUCUUUGG (SEQ ID NO:15), and CUGAAGAAAGCAUUGACUA (SEQ ID NO:16). siRNAa useful in silencing expression of p85α include GGAAAUAUGGCUUCUCUGAUU (SEQ ID NO:9), GAAAGACGAGAGACCAAUAUU (SEQ ID NO:10), GUAAAGCAUUGUGUCAUAAUU (SEQ ID NO:11), and UGGCUUCUCUGACCCAUUAUU (SEQ ID NO:12). The control siRNA used in these experiments was purchased from Dharmacon Inc. TransIT In Vivo Gene Delivery System was purchased from Mirus (Madison, Wis.) Lipofectamine 2000 transfection reagent was obtained from Invitrogen (Carlsbad, Calif.). Rabbit anti-Akt, phospho (Ser473) and anti-p110α were purchased from Cell Signaling (Beverly, Mass.). Mouse monoclonal anti-p85α antibody was purchased from Upstate (Charlottesville, Va.). Mouse monoclonal anti-β-actin antibody was obtained from Sigma-Aldrich (St. Louis, Mo.). pEGFP vector was obtained from Clontech Laboratories (Mountain View, Calif.). Immobilon P membranes for Western blots were from Millipore Corp. (Bedford, Mass.), and x-ray film was purchased from Eastman Kodak (Rochester, N.Y.). The enhanced chemiluminescence (ECL) system for Western immunoblot analysis was from Amersham Biosciences (Arlington Heights, Ill.). All other reagents were of molecular biology grade and purchased from Sigma-Aldrich.

Tissue Procurement. Primary colorectal adenocarcinomas and adjacent mucosa (approximately 5-10 cm from the cancer) were obtained from 40 patients undergoing elective surgical resection over a 4-year period from 2001 to 2005 at the University of Texas Medical Branch (UTMB), Galveston, Tex. Tumor stage (TNM classification, Macdonald and Struhl, Nature. 324:537-545 (1986)) and differentiation grade were assessed. Immediately upon collection, samples were placed in liquid nitrogen and stored at −80° C. until used for immunohistochemistry.

Immunohistochemistry. Samples (paired colorectal cancers or polyps and adjacent normal mucosa) were removed from −80° C. and placed into 10% neutral buffered formalin for 24 hours, then into 70% ethanol for 24 hours. Formalin-fixed tissues were embedded in paraffin, and sections (5 μm) were cut from the paraffin blocks. The sections were deparaffinized in xylene and rehydrated in descending ethanol series. Protein staining was performed using DAKO EnVision Kit (Dako Corp., Carpinteria, Calif.). Briefly, sections were incubated overnight at 4° C. with monoclonal antibodies (diluted 1:100 in 0.05 mol/L Tris-HCL+1% BSA) against p85α (Santa Cruz Biotechnology, Santa Cruz, Calif.), Akt1, Akt2, p110α, and PTEN (Cell Signaling). After 3 washes with TBST, the sections were incubated for 30 minutes with secondary antibody labeled with peroxidase, then washed 3 times with TBST. Lastly, peroxidase substrate DAB was added for staining. All sections were counterstained with hematoxylin and observed by light microscopy. For negative controls, primary antibody was omitted from the above protocol.

Transfection Techniques. siRNA directed against p85α and p110α, and nontargeting control (NTC) were introduced into HT29 and KM20 cells by electroporation (Gene Pulser, Bio-Rad). Exponentially growing cells ($3 \times 10^6$) were resuspended in culture medium without FCS, supplemented with 20 mmol/L HEPES and electroporated with siRNA (100 nmol). The conditions of electroporation were: 400 V and 500 μF for HT29; 300 V and 600 μF for KM20. Lipofectamine 2000 transfection reagent was used to transfect HT29 cells with the GFP vector for assessment of in vivo metastasis. Briefly, Lipofectamine 2000 transfection reagent and GFP:DNA vector were incubated for 5 minutes in serum-free media and then mixed together for 20 minutes at room temperature. The DNA mixture was applied to HT29 cells for 4 hours at 37° C. in serum-free media. After incubation, FBS was added to a final concentration of 10%. Cells were grown in 37° C. and 5% $CO_2$, and the culture media was changed daily. After 4 days, cells were selected using G418 antibiotic (500 μg/mL), and transfected clones were identified by FACS A219 cell sorter on the basis of GFP fluorescence. GFP expression was ~35% as determined by fluorescence-activated cell sorting.

Protein Preparation and Western Immunoblot. Western immunoblot analyses were performed as described previously (Wang et al., Clin Cancer Res. 8:1940-1947 (2002)). Cells were lysed with TNN buffer at 4° C. for 30 minutes. Lysates were clarified by centrifugation (10,000 g for 30 minutes at 4° C.) and protein concentrations determined using the method of Bradford (Bradford, Anal Biochem., 72:248-254 (1976)). Briefly, total protein (60 μg) was resolved on a 10% polyacrylamide gel and transferred to Immobilon-P nylon membranes. Filters were incubated overnight at 4° C. in blotting solution (Tris-buffered saline containing 5% nonfat dried milk and 0.1% Tween 20), followed by a 1-hour incubation with primary antibodies. Filters were washed 3 times in a blocking solution and incubated with horseradish peroxidase-conjugated secondary antibodies for 1 hour. After 3 additional washes, the immune complexes were visualized by ECL detection.

MTT Assay. Forty-eight hours after p85α, p110α, or NTC siRNA transfection, adherent cells were detached by rapid trypsinization, counted in a Hausser chamber, and replated into 96-well plates at a concentration of $1 \times 10^3$ cells/well. Assays were performed at 48, 72, 96, 120, and 144 hours posttransfection according to the manufacturer's protocol and as previously described (Iwase et al., Cancer, 79:1787-1793 (1997)).

Apoptosis Assays. Cells were replated in 96-well plates at 96 hours posttransfection; APOPercentage Dye uptake during the apoptotic process was measured the next day with APOPercentage APOPTOSIS Assay kit (Accurate Chemical & Scientific, Westbury, N.Y.) according to manufacturer's instructions. DNA fragmentation was quantified by determination of cytoplasmic histone-associated DNA fragments (mono- and oligonucleosomes) using a Cell Death Detection ELISA$^{Plus}$ kit (Roche Molecular Biochemicals) according to the manufacturer's instructions and as previously described (Wang et al., Clin Cancer Res. 8:1940-1947 (2002)).

In Vivo Experiments. For in vivo studies, 4- to 6-week-old male nude$^{nu/nu}$ mice were obtained from Harlan Sprague Dawley (Indianapolis, Ind.) and housed in clean, pathogen-free rooms in an environment with controlled temperature (22° C.), humidity, and a 12 hours light/dark cycle. The mice were fed standard chow (Formula Chow 5008; Purina Mills, St. Louis, Mo.) and tap water ad libitum and allowed to acclimate for 1 week. All studies were approved by the Institutional Animal Care and Use Committee of UTMB. Tumor cells were injected intrasplenically by methods previously described (Bruns et al., Neoplasia, 1:50-62 (1999)). Briefly, mice were anesthetized with halothane, a small left abdominal flank incision was created, and the spleen was exteriorized. Transfectants were harvested using only trypsin and resuspended as a single-cell suspension in Hanks Balanced Salt Solution, free of $Mg^{2+}$ and $Ca^{2+}$. Tumor cells ($5 \times 10^6$ cells/400 μL) were injected into the spleen with a 27-gauge needle. The spleen was returned to the abdomen, and the wound was closed in one layer with wound clips. The mice were observed over the indicated time period using the Illumatool TLS (Lightools Research, Encinitas, Calif.). Animals were randomized into 3 experimental groups (5 animals per group) to receive p85α, p110α, or NTC siSTABLE siRNA (20 μg/mice, qod) by hydrodynamic tail vein injection (Watanabe et al., Gastroenterology, 128:1391-1404 (2005)) 24 hours after operation; mice were killed 35 days later. Experiments were performed in duplicate.

Statistical Analysis. DNA fragmentation for HT29 or KM20 and ADP analysis were analyzed using one-way classification analysis of variance. The group (NTC, p85α, and p110α) was assessed at the 0.05 level of significance. Fisher's least significant difference procedure was used for multiple comparisons with Bonferroni adjustment for the number of comparisons. The effect of siRNA on cell growth was analyzed with the Kruskal-Wallis test. A P value of 0.05 was considered significant.

Results

Expression of the PI3K p85α Regulatory Subunit, Akt2, and PTEN in Human Colorectal Polyps, Cancers, and Corresponding Normal Mucosa. Colorectal cancers and adjacent normal mucosa from 40 patients with either proximal (i.e., cecal or ascending colon) or distal (ie, sigmoid or rectal)

tumors were analyzed for expression of the PI3K/Akt pathway components p85α and p110α, Akt1, and Akt2, and the tumor suppressor PTEN, the natural PI3K inhibitor (Table 1) shows patient characteristics, tumor location, and TNM staging (Hermanek et al., *Rontgenblatter.* 40:200 (1987)). In our current study, we have focused our comparison on proximal and distal cancers due to previous findings noting a differential expression pattern of PTEN with decreased expression in the distal colon (Kim et al., *Cancer Chemother Pharmacol.*, 50:343-352 (2002); Di Cristofano et al., *Nat. Genet.*, 19:348-355 (1998)). Three patients had resections for tubulovillous adenomas. PTEN, p85α, and Akt2 expression was highest in the surface epithelium of normal colon, with PTEN expression extending into the base of the crypts; PTEN expression was more pronounced than either p85α or Akt2. The glandular elements of the polyps expressed PTEN, p85α, and Akt2, with p85α expression stronger than either PTEN or Akt2; p85α and Akt2 expression in the stroma was limited to endothelium and inflammatory cells, with a predominantly cytoplasmic distribution, while there was a predominantly nuclear distribution of PTEN by fibroblasts and inflammatory cells in the stroma. Thus, in contrast to the adjacent normal mucosa, the polyps expressed higher levels of p85α and Akt2.

TABLE 1

Patient Demographics

| Demographic | Value |
|---|---|
| Age (yr) | |
| Mean | 64.0 |
| Range | 26-87 |
| Sex | |
| Male | 17 |
| Female | 23 |
| Site | |
| Right colon | 23 |
| Rectosigmoid | 17 |
| Race | |
| White | 23 |
| Black | 11 |
| Hispanic | 6 |
| TNM classification | |
| Stage 0 | 3 |
| Stage I | 6 |
| Stage II | 11 |
| Stage III | 15 |
| Stage IV | 5 |

Stage I, stage II, and stage III colorectal cancers were analyzed. Similar expression patterns were noted for these cancers. Similar to the normal adjacent mucosa from patients with polyps, PTEN and p85α expression was highest in the surface epithelium with some expression noted in inflammatory cells in the superficial lamina propria; Akt2 expression was again limited to the surface epithelium. In contrast to the glandular elements of polyps, the glandular elements of the stage I, II, and III cancers expressed little to no PTEN, but strongly expressed p85α and Akt2 with a similar distribution and intensity. There was little to no PTEN expression in the stroma, with p85α and Akt2 expression again limited to stromal endothelium and inflammatory cells.

Five patients presented with liver metastasis (stage IV disease). Compared with sections of normal mucosa from patients with polyps or stage I, II, or III cancers, which demonstrated predominant PTEN and p85α expression with little Akt2 expression, there was little to no PTEN expression in the surface epithelium of normal colon or lamina propria, with strong expression of both p85α and Akt2 in the surface epithelium descending into the base of the crypts. In the cancers, there was little to no PTEN expression in the glandular or stromal elements, but strong expression of both p85α and Akt2 in the glandular elements, and a similar cytoplasmic distribution of p85α and Akt2 in inflammatory cells and stromal endothelium. Akt2 expression was more pronounced in stage IV disease than in any other stage.

Overall, there were no apparent differences in the expression patterns of proximal or distal colorectal cancers. Consistent with previous studies (Di Cristofano et al., *Nat. Genet.*, 19:348-355 (1998); Kim et al., *Gastroenterology*, 123:1163-1178 (2002)), an increase in PTEN expression was noted in the normal proximal colonic mucosa compared with the normal distal (ie, rectosigmoid) mucosa. Expression of Akt1 was variable, with expression noted in some polyps and stage I and II cancers. Little p110α expression was demonstrated in either the normal colonic mucosa or the cancers. Collectively, our findings suggest increased expression of p85α and Akt2 in stage I, II, and III colorectal cancers compared with normal mucosa or benign polyps; this expression pattern appeared stronger in stage IV cancers where there also appeared to be increased p85α and Akt2 expression in the normal adjacent mucosa compared with normal mucosa of patients with stages I, II, and III cancers. PTEN expression was decreased in all cancers compared with polyps or normal mucosa.

p85α and p110α siRNA Decrease In Vitro Colon Cancer Cell Survival and Increase Apoptosis in Human Colon Cancer Cells KM20 and HT29 PI3K inhibition exhibits a potent antitumor effect in certain cancer cells including colon cancers (Wang et al., *Clin Cancer Res.* 8:1940-1947 (2002); Osaki et al., *Apoptosis*, 9:667-676 (2004); these effects appear to be due to inhibition of Akt/PKB phosphorylation (Itoh et al,. *Cancer*, 94:3127-3134 (2002)). To determine the functional effects of RNAi treatment, the effect of siRNA treatment on the viability of KM20 and HT29 cells was examined by MTT assay (FIG. 1). Transfection with either p85α or p110α siRNA significantly suppressed cell viability in KM20 (FIG. 1A) and HT29 (FIG. 1B) cells at 120 and 144 hours after transfection compared with NTC. To confirm inhibition of expression by siRNA treatment, protein was extracted and analyzed by Western blot (FIG. 1C, 1D). Transfection with siRNA directed to either p85α or p110α into KM20 cells (FIG. 2C) or HT29 (FIG. 1D) reduced p85α and p110α protein levels, respectively, at 120 hours after transfection. Both p85α and p110α siRNA suppressed basal pAkt expression.

Figure 2:
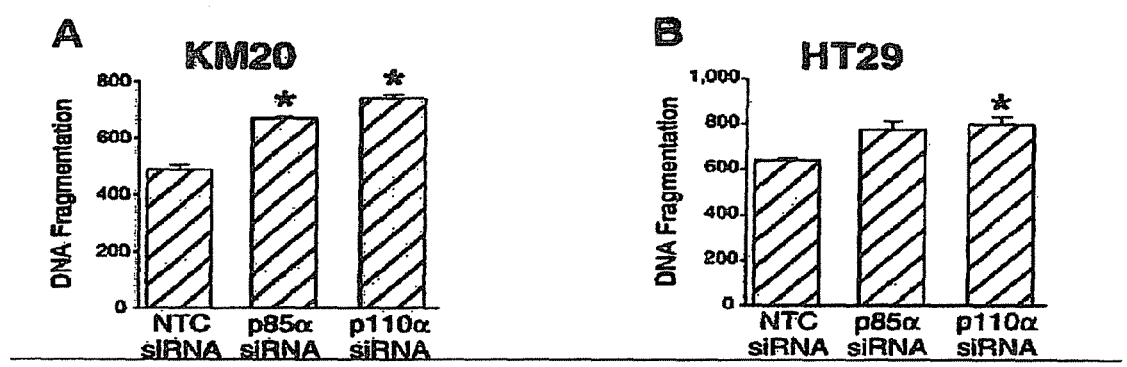
FIG. 2. siRNA directed against p85α or p110α increases apoptosis. KM20 or HT29 cells were transfected with siRNA (100 nmol) directed against p85α, p110α, or nontargeting control (NTC) as described in Materials and Methods, and 72 hours posttransfection seeded in 96-well plates. Quantitative in vitro determination of cytoplasmic histone-associated DNA fragments was performed using a Cell Death Detection ELISA$^{PLUS}$ in KM20 (C) and HT29 (D) cells. Data represent mean±SD. *$P<0.05$ versus NTC. †$P<0.05$ versus p85α siRNA or p110α siRNA alone.

To determine whether this reduction in cell viability was a result of increased cell death, apoptosis was analyzed by 2 methods (FIG. 2). In the first, APOPercentage Dye uptake was measured after the various treatments with APOPercentage APOPTOSIS Assay kit. The APOPercentage Dye enters the cells following phosphatidylserine transmembrane movement; dye uptake continues until blebbing occurs. No further dye can then enter the cell, and dye that has accumulated within the cell is not released. An increase in APOPercentage Dye uptake was demonstrated in both KM20 and HT29 colon cancer cells treated with either p85α or p110α siRNA compared with NTC. In the second method, DNA fragmentation was measured by an ELISA assay (FIG. 2A, 2B). An increase in DNA fragmentation, which is characteristic of apoptosis, was demonstrated in both KM20 and HT29 colon cancer cells with either p85α or p110α siRNA compared with NTC. In HT29 cells, treatment with p110α siRNA achieves statistical significance. Even though siRNA to p85α and p110α increased apoptosis, the increase in cell death was not as dramatic as previously noted with other agents (eg, wortmannin, which irreversibly inhibits PI3K) (Krystal et al., *Mol Cancer Ther.*, 1:913-922 (2002)). Therefore, the effect of targeted treatment of PI3K components may be more directed to tumor cell suppression.

Figure 3:
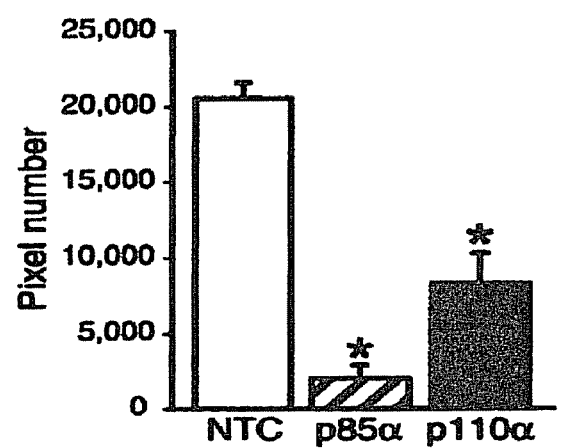
FIG. 3. Suppression of metastatic tumor growth by p85α or p110α siRNA. A, HT29-GFP cells ($5 \times 10^6$) were inoculated intrasplenically and mice were killed 5 weeks later. Animals were monitored individually for metastatic tumor growth using the Illumatool TLS. Animals were randomized into 3 experimental groups (5 animals per group) to receive p85α, p110α, or nontargeting siSTABLE siRNA (20 μg/mice, qod) by hydrodynamic tail vein injection 24 hours after intrasplenic injection; mice were killed 35 days later. Using Adobe Photoshop, the level of fluorescence was measured and expressed as a pixel number. All tests were assessed at the 0.05 level of significance.

Suppression of Metastatic Tumor Growth by p85α or p110α siRNA Treatment. The liver is a common site of systemic metastases from colorectal cancer (Jemal et al., *CA Cancer J Clin.*, 53:5-26 (2003)). The involvement of the PI3K pathway has been linked to tumor cell migration and invasion in a number of cancers through multiple mechanisms (Itoh et al,. *Cancer,* 94:3127-3134 (2002); Samuels et al., *Cancer Cell.*, 7:561-573 (2005)), suggesting that this signaling pathway may contribute to invasion and metastasis in colorectal cancers. To begin to analyze the effects of siRNA treatment on colorectal cancer metastasis to the liver, a liver metastasis model was established using described techniques that involve injection of colorectal cancer cells into the spleen of athymic mice (Bruns et al., *Neoplasia,* 1:5062 (1999)). Pilot studies were performed to establish the optimal conditions that would provide detectable liver metastases in all mice but not too numerous so that any treatment differences could be observed; HT29 cells ($5 \times 10^6$) injected intrasplenically were noted to be optimal in our system. In addition, HT29 cells were transfected with a plasmid containing GFP, which allows for a real-time assessment of tumor metastasis using the Illumatool TLS (FIG. 3). Typically, metastases to the liver are detected 3 to 4 weeks after splenic injection. Using this model, it was next determined whether intravenous siRNA injection directed against p85α or p110α could alter the metastasis of HT29 cells to the liver. Tumor cells were injected into the spleen by methods previously described (Bruns et al., *Neoplasia,* 1:50-62 (1999)). Animals were randomized into 3 experimental groups (5 animals per group) to receive p85α, p110α, or nontargeting siSTABLE siRNA (20 µg/mice, qday) by hydrodynamic tail vein injection (Song et al., *Nat. Med.,* 9:347-351 (2003); Zhang et al., *Hum Gene Ther.* 10:1735-1737 (1999)) starting 24 hours after intrasplenic tumor injection; mice were killed 35 days later. The development of liver metastasis was monitored in vivo by bioluminescent imaging. Mice treated with NTC siRNA demonstrated increased metastases compared with either the p85α or p110α a siRNA-treated groups as noted by a qualitative assessment of GFP fluorescence; treatment with p85α siRNA appeared to be more effective than p110α siRNA. Results were further quantified by measurement of fluorescence and values expressed as pixel numbers (FIG. 3). Results demonstrate a significant decrease in tumor metastasis in the p85α and p110α siRNA-treated groups compared with NTC which correlates with our qualitative assessment. Therefore, systemic delivery of PI3K-specific siRNA could represent a unique strategy for the suppression of colorectal cancer metastasis.

Discussion

Activation of the PI3K/Akt pathway increases proliferation and cell survival of certain cancers, including colorectal cancers (Fresno Vara et al., *Cancer Treat. Rev.,* 30:193-204 (2004); Itoh et al,. *Cancer,* 94:3127-3134 (2002)). Previously, it has been demonstrated that inhibition of PI3K, using the chemical inhibitors wortmannin or LY294002, enhanced sodium butyrate (NaBT)-induced colorectal cancer apoptosis in vitro and suppressed growth of xenograft tumors (Wang et al., *Clin Cancer Res.* 8:1940-1947 (2002)). Moreover, it has recently been shown that targeted RNAi to PI3K/Akt components, particularly p85α, can sensitize resistant colorectal cancers to TRAIL-mediated apoptosis (Rychahou et al., *Surgery,* 138:391-397 (2005)). In this study, these previous findings have been extended and demonstrate the following important points: 1) expression of p85α and Akt2 are increased in the glandular components of human colorectal cancers of all stages compared with polyps and normal mucosa; PTEN protein expression was decreased in these cancers, 2) treatment of colon cancers in vitro with siRNA directed to the p85α or p110α genes suppressed cell growth, and 3) using a murine model of colorectal cancer metastasis, siRNA directed to either p85α or p110α significantly suppressed tumor metastases. This study provides additional evidence that selective targeting of PI3K components, such as p85α, may provide a novel treatment strategy for colorectal cancers. This strategy may prove useful in the treatment of colorectal cancers either to increase tumor cell death or, more likely, to enhance the sensitivity of chemoresistant cancers to the effects of other chemotherapeutic agents.

Class I PI3Ks are heterodimers composed of a regulatory (p85) and catalytic (p110) subunit; the regulatory p85 subunit is essential for the stability of the p110 catalytic subunit and for its recruitment to activated growth factor receptors (Yu et al., *Mol Cell Biol.,* 18:1379-1387 (1998)). Previous studies have suggested a role for the p85α subunit in colorectal cancers (Rychahou et al., *Surgery,* 138:391-397 (2005)); other investigators have shown that the p110 subunit likewise plays an important role in colorectal cancers (Ikenoue et al., *Cancer Res.,* 65:4562-4567 (2005)). In this study, immunohistochemical analyses of cancers or polyps and adjacent normal mucosa of 40 patients have been performed to assess expression of PI3K pathway components. The data demonstrate increased p85α expression in the glandular elements of colorectal cancers at all stages. An increasing role for the surrounding stroma in tumorigenesis has been proposed (Micke and Ostman, *Exp. Opin. Ther. Targets,* 9:1217-1233 (2005)). In this regard, we also noted p85α expression within the cytoplasm of endothelial cells and inflammatory cells present within the stroma. This is in marked contrast to the normal mucosa of patients with stage I, II, and III cancers, where p85α expression was limited to the surface epithelium, with little p85α expression in inflammatory cells present in the superficial lamina propria. Interestingly, increased p85α expression was noted in the normal mucosa of patients with stage IV cancers. These results are in agreement with findings in breast cancers, where a majority of the cancers exhibit increased p85α expression (Gershtein et al,. *Clin. Chim. Acta,* 287:59-67 (1998)), and in agreement with studies that have identified p85α/PI3K overactivity in approximately 86% of colorectal cancer specimens when compared with matched normal controls (Phillips et al., *Cancer,* 83:41-47 (1998)). We found little expression of p110α in cancers or normal mucosa which further supports a role for the increased expression of the p85α subunit in the growth or invasive properties of colorectal cancers. p110α is amplified in colon, gastric, lung, brain, breast cancers. But it is not the primary mutation in these cancers (Karakas et al., *Br. J. Cancer,* 94:455-459 (2006)).

We next assessed expression of the Akt1 and Akt2 isoforms, which are activated by upstream PI3K, and subsequently activate a number of proteins critical for cell growth or survival (Roy et al., *Carcinogenesis,* 23:201-205 (2002)). Previous studies have identified increased expression of phosphorylated Akt1 and Akt2 in colorectal cancers and colon cancer cell lines (Khaleghpour et al., *Carcinogenesis,* 25:241-248 (2004); Roy et al., *Carcinogenesis,* 23:201-205 (2002)). Because of the variable delay between the time of tumor resection and sample collection, we did not examine the expression of the labile phosphorylated Akt, concentrating instead on Akt1 and Akt2 distribution. A number of studies have focused on the role of Akt1 as the important isoform for PI3K-mediated cell proliferation (Hutchinson et al., *Cancer Res.*, 64:3171-3178 (2004)); however, the demonstration of Akt1 expression was highly variable in our study, with minimal expression noted in many cancers. In contrast, these findings clearly showed increased Akt2 expression in all colorectal cancers, particularly in the stage IV cancers. Similar to the increased p85α expression in the adjacent normal mucosa of patients with stage IV cancers, Akt2 expression was also increased. Increasingly, studies are suggesting a more prominent role for Akt2 expression in cancer invasion. For example, Akt2 overexpression contributes to the up-regulation of β1 integrins and increased invasion and metastasis in human breast, ovarian, and colorectal cancers (Roy et al., *Carcinogenesis*, 23:201-205 (2002); Arboleda et al., *Cancer Res.*, 63:196206 (2003)).

The PTEN protein plays an important role in the carcinogenesis of multiple human cancers including colorectal cancers (Guanti et al., *Hum Mol Genet.*, 9:283-7 (2000)). PTEN modulates cell growth and survival by negatively regulating PI3K/Akt, leading to cell cycle inhibition (Cantley and Neel, *Proc Natl Acad Sci USA*, 96:4240-4245 (1999)). PTEN expression was decreased in the colorectal cancers compared with expression in polyps and normal mucosa. This is consistent with evidence suggesting that PTEN expression is decreased in approximately 40% of colorectal cancers, often with associated PTEN mutation or deletion (Goel et al., *Cancer Res.*, 64:3014-3021 (2004)). In addition to colorectal cancers, decreased PTEN expression has been demonstrated in other cancers, most notably breast and prostate cancers (Li et al., *Science*, 275:1943-1947 (1997)). Finally, these data confirm findings of decreased PTEN expression in the distal colon and rectum, which was previously noted in animal studies (Kim et al., *Gastroenterology*, 123:1163-1178 (2002)). It is interesting to speculate that decreased PTEN expression may contribute to the propensity for cancers in the more distal colon and rectum.

The PI3K pathway and downstream proteins are increasingly recognized as potential targets for anticancer therapies. For example, mammalian target of rapamycin (mTOR) kinases are among the downstream targets of Akt and are thought to link mitogenic stimulation to protein synthesis and cell cycle regulation (Shao et al., *Cancer Res.*, 64:229-235 (2004); Liu et al., *Anticancer Res.*, 24:2697-2704 (2004)). Several rapamycin analogs (eg, CCI-779 and RAD001) are currently being evaluated in clinical trials to test efficacy against certain cancers (Chan et al., *J. Clin. Oncol.*, 23:5314-5322 (2005); Raymond et al., *J Clin Oncol.*, 22:2336-2347 (2004)). Kinase inhibitors targeting Akt or PDK1 are being developed but, thus far, lack specificity (Davies et al., *Biochem. J.*, 351(Pt 1):95-105 (2000)). Another approach used in experimental models is to broadly inhibit PI3K using either LY294002 or wortmannin. LY294002 can inhibit the growth of certain cancers, including colorectal cancer (Semba et al., *Clin. Cancer Res.*, 8:1957-1963 (2002)) in in vivo experimental models; however, usage is limited by the toxicity of the agent. In addition, it has been shown (Wang et al., *Clin Cancer Res.* 8:1940-1947 (2002); Ng et al., *Clin. Cancer Res.*, 7:3269-3275 (2001)) that wortmannin treatment inhibits the in vivo growth of cancers through the irreversible inhibition of PI3K (Powis et al., *Cancer Res.*, 54:2419-2423 (1994)). However, the ubiquitous expression and function of PI3K will likely prevent the use of global inhibitors for chronic treatment, since these inhibitors (especially wortmannin) exert a significant nonspecific toxicity (Davies et al., *Biochem. J.*, 351 (Pt 1):95-105 (2000)), precluding use as anticancer agents in patients. A more targeted approach to PI3K inhibition may allow for more effective and less toxic side effects.

Two potential targets include the p110 catalytic subunit, which promotes cell growth and invasion of human cancer cells (Samuels et al., *Cancer Cell.*, 7:561-573 (2005)), and the p85 regulatory subunit, which can activate class Ia PI3K by receptor tyrosine kinases (Jimenez et al., *J. Biol. Chem.*, 277:41556-41562 (2002)). This study shows that siRNA directed to either p110α or p85α effectively suppressed colon cancer cell growth in vitro through mechanisms that include increased cell death. Consistent with the inhibition noted by p110α siRNA, Takeshita et al. (Takeshita et al., *Proc. Natl. Acad. Sci., USA*, 102:12177-12782 (2005)) noted inhibition of prostate cancer proliferation in vitro and metastatic tumor growth after p110α siRNA treatment. Interestingly, the inhibition of p85α may prove to be a more selective form of therapy. Recent studies showed that p85α forms a complex with a protein network associated with oncogenic fusion tyrosine kinases (FTKs) (eg, BCR/ABL, TEL/ABL, TEL/JAK2, TEL/PDGFβR, and NPM/ALK) resulting in constitutive activation of the p110 catalytic subunit of PI3K. These results suggest that the BCR/ABL-p85 association may be a potential target for small molecules designed to disassemble/prevent this interaction and stop malignant growth (Ren et al., *Mol. Cell. Biol.*, 25:8001-8008 (2005)).

To further determine the potential efficacy of this RNAi approach in the treatment of colorectal cancer, we used a clinically relevant in vivo model of liver metastasis injecting colon cancer cells into the spleen of athymic nude mice as has been described previously (Bruns et al., *Neoplasia*, 1:50-62 (1999)). Intravenous injection of either p85α siRNA or p110α siRNA significantly suppressed liver metastasis with p85α siRNA appearing to be more effective in this regard. These findings show that therapies targeting the p85α or p110α subunits may be useful in the armamentarium of agents to suppress cancer growth and metastasis. Consistent with our current study, which suggests possible beneficial effects of selective RNAi in the treatment of colorectal cancer, recent studies, using other cancer models, have shown encouraging results. For example, siRNA targeting VEGF effectively inhibits growth of malignant melanoma and squamous cell carcinoma of head and neck cancers both in vitro and in vivo (Tao et al., *Br. J. Dermatol.*, 153:715-724 (2005); Zhang et al., *Clin. Cancer Res.*, 11:6261-6269 (2005)). Also, down-regulation of antiapoptotic gene expression (eg, survivin) by in vivo siRNA can decrease the radioresistance of breast cancer cells (Uchida et al., *Molecular Therapy.* 10:162 (2004)).

RNAi has the potential to be more selective and, as a result, more effective and less toxic than traditional approaches. Proprietary chemical modifications have been developed that dramatically enhance both the stability and silencing longevity of siRNA while improving its potency and decreasing cellular toxicity (Chiu and Rana, *RNA*, 9:1034-1048 (2003)). These modifications now enable studies that were previously not feasible due to instability of the siRNA duplex or short duration of siRNA-mediated silencing and may provide for agents that are more clinically applicable for treating disease states that require longer acting effects.

EXAMPLE 2

Materials and Methods

Methods of cells transfection and liver metastasis establishment are described in Example 1.

Cell proliferation was measured using the sulforhodamine B (SRB) calorimetric assay (Skehan et al., *J. Natl. Cancer*

*Inst.*, 82 (13):1107 (1990)). Briefly, 15×10³ cells were seeded in a 96-well microtiter plate. At various times, cells were fixed in 10% trichloroacetic acid for 1 h at 4° C., rinsed and subsequently stained for 30 min at room temperature with 0.2% SRB dissolved in 1% acetic acid, followed by air drying. The bound dye was solubilized in 100 µl of 10 mM unbuffered Tris base for 30 min and the OD was read at 490 nm in an ELISA plate reader.

Results

Figure 4:
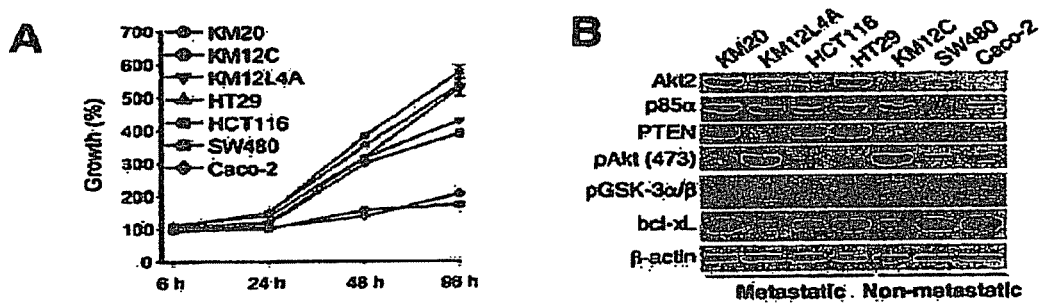
FIG. 4. AKT2 is expressed at high levels in metastatic colorectal cell lines. A. CRC cells ($1 \times 10^6$) were plated in 6 well plates, and cell proliferation was measured using the sulforhodamine B colorimetric assay. B. Total cell lysates were prepared and equivalent amounts of protein were resolved by SDS-PAGE, blotted, and probed with indicated antibodies.

Having observed Akt2 increase in late stage colorectal cancer, we asked if this regulation is seen in vitro. We examined 4 metastatic human colorectal carcinoma cell lines (KM20, HT29, HTC116 and KM12L4A) and 3 nonmetastatic human colorectal carcinoma cell lines (KM12C, SW480, Caco-2) for Akt2 expression, in which it might play a role in the invasive or metastatic phenotypes. An analysis of endogenous Akt2 expression in a variety of colorectal cell lines demonstrated elevated expression of Akt2 in highly metastatic cell lines KM20 and HT29 (FIG. 4 B). When compared with the parental KM12C cell line, KM12L4A exhibited an increase in Akt2 protein levels. Because AKT2 activity is known to be dependent on PI3K activity, the cellular expression level of the PTEN phosphatase and basal AKT phosphorylation were also determined for these cells.

Figure 5:
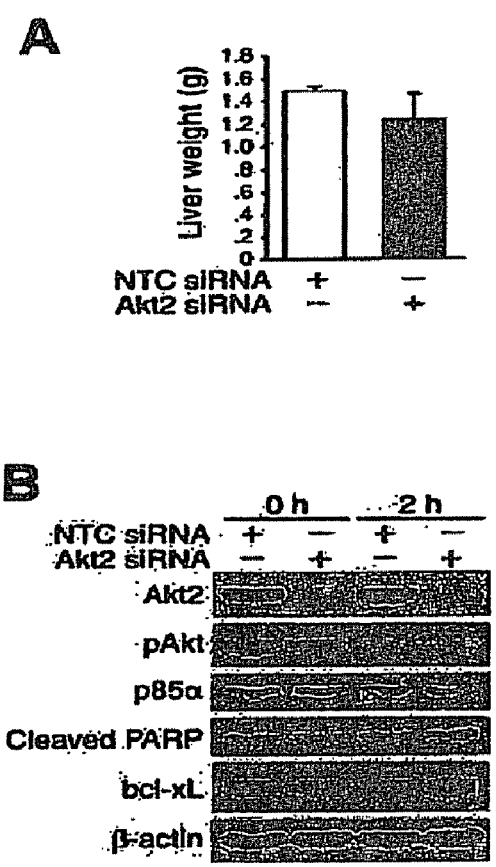
FIG. 5. Suppressed HT29 liver metastasis establishment after Akt2 downregulation. HT29-GFP cells were transfected with NTC or Akt2 siRNA in vitro, inoculated intrasplenically ($5 \times 10^6$) 60 h later. To avoid intrasplenic tumor growth, the spleen was removed after 24 h. Animals were monitored individually for metastatic tumor growth using the Illumatool TLS and sacrificed 21 d after intrasplenic inoculation. A. Liver weights (NTC, n=4; Akt2 P=0.2996). B. Western blot analysis of the cells used for intrasplenic inoculation before (0 h) or after (2 h) surgical procedure.
Figure 6:
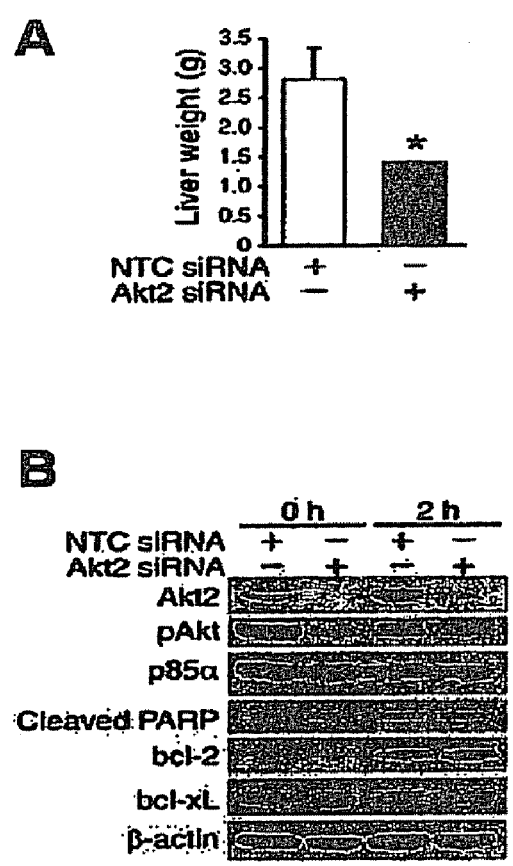
FIG. 6. Suppressed KM20 liver metastasis establishment after Akt2 downregulation. KM20-GFP cells were transfected with NTC or Akt2 siRNA in vitro, inoculated intrasplenically ($5 \times 10^6$) 60 h later. To avoid intrasplenic tumor growth, the spleen was removed after 24 h. Animals were monitored individually for metastatic tumor growth using the Illumatool TLS and sacrificed 21 d after intrasplenic inoculation. A. Liver weights (NTC, n=4; Akt2, n=4; P=0.0351). B.

Akt2 is essential for colorectal cancer metastasis establishment. To determine whether Akt2 plays a causal role in colorectal cancer metastasis, we tested whether inhibition of Akt2 expression in the highly metastatic colorectal cancer cells would affect their metastatic ability. HT29$^{GFP}$ or KM20$^{GFP}$ cells were transfected with NTC (purchased from Dharmacon Inc.) or Akt2 siRNA (GUACUUC-GAUGAUGAAUUU, SEQ ID NO:20) in vitro and inoculated intrasplenically (5×10⁶) 60 hours later. To avoid intrasplenic tumor growth, the spleen was removed after 24 h. Animals were monitored individually for metastatic tumor growth using the Illumatool TLS. Three weeks after implantation the mice were sacrificed and the liver was examined for metastatic lesions by inspection of GFP fluorescence. While cells transfected with NTC siRNA formed large numbers of macroscopically visible metastases in their livers, those that were transfected with Akt2 siRNA formed very few metastases. Histological analysis confirmed that the number of micrometastatic lesions was also drastically reduced in the livers of Akt2 siRNA group. In addition, the sizes of individual metastatic nodules present in the liver of both groups of mice were very similar. These results suggested that transient loss of Akt2 expression reduced the number of metastatic nodules present in the liver, rather then preventing micrometastases established in the liver from proliferating into visible nodules. We also suspect that incomplete suppression of Akt2 by siRNA in a small subset of cells account for the residual ability of such cells to form liver metastasis. Western blot analysis of the cells used for intrasplenic inoculation confirmed Akt2 downregulation (FIG. 5-6 B).

The complete disclosure of all patents, patent applications, and publications, and electronically available material (including, for instance, nucleotide sequence submissions in, e.g., GenBank and RefSeq, and amino acid sequence submissions in, e.g., SwissProt, PIR, PRF, PDB, and translations from annotated coding regions in GenBank and RefSeq) cited herein are incorporated by reference. In the event that any inconsistency exists between the disclosure of the present application and the disclosure(s) of any document incorporated herein by reference, the disclosure of the present application shall govern. The foregoing detailed description and examples have been given for clarity of understanding only. No unnecessary limitations are to be understood therefrom. The invention is not limited to the exact details shown and described, for variations obvious to one skilled in the art will be included within the invention defined by the claims.

All headings are for the convenience of the reader and should not be used to limit the meaning of the text that follows the heading, unless so specified.

What is claimed is:

1. A method for treating a metastatic cancer in a subject comprising administering to a subject having a metastasis of a primary cancer an effective amount of a double stranded polynucleotide that suppresses expression of an Akt2 polypeptide, wherein treatment of the metastatic cancer is after the occurrence of the metastatic cancer.

2. The method of claim 1 wherein the polynucleotide comprises SEQ ID NO:20.

3. The method of claim 1 wherein the primary cancer is selected from colorectal cancer, breast cancer, and lung cancer.

4. The method of claim 1 wherein the primary cancer is colorectal cancer.

5. The method of claim 1 wherein the metastatic cancer is located in a lymph node.

6. The method of claim 1 wherein the metastatic cancer is located in the liver.

7. A method for treating cancer in a subject comprising administering to a subject having a metastasis of a colorectal cancer an effective amount of a double stranded polynucleotide that suppresses expression of an Akt2 polypeptide, wherein the subject has colorectal cancer.

8. The method of claim 7 wherein the polynucleotide comprises SEQ ID NO:20.

9. A method for treating cancer in a subject comprising:
administering to a subject an effective amount of a polynucleotide, wherein the subject has a metastasis of a colorectal cancer, wherein the polynucleotide comprises a sense strand and an antisense strand, wherein the sense strand comprises a nucleotide sequence of between 19 and 29 nucleotides, and wherein the nucleotide sequence is substantially identical to consecutive nucleotides of a target mRNA encoded by an akt2 coding region.

10. The method of claim 9 wherein the polynucleotide comprises SEQ ID NO:20.

* * * * *

UNITED STATES PATENT AND TRADEMARK OFFICE
CERTIFICATE OF CORRECTION

PATENT NO. : 8,198,252 B2  
APPLICATION NO. : 12/301387  
DATED : June 12, 2012  
INVENTOR(S) : Evers et al.

It is certified that error appears in the above-identified patent and that said Letters Patent is hereby corrected as shown below:

On the Title page, Item (12), under the header, delete "Evans et al." and insert -- Evers et al. --;

On the Title page, Item (75), under Inventors (first column), delete "B. Mark Evans" and insert -- B. Mark Evers --;

In column 23, line 17, delete "196206" and insert -- 196-206 --.

Signed and Sealed this
Twenty-sixth Day of February, 2013

Teresa Stanek Rea
*Acting Director of the United States Patent and Trademark Office*

```
                       SEQUENCE LISTING

<160> NUMBER OF SEQ ID NOS: 20

<210> SEQ ID NO 1
<211> LENGTH: 2074
<212> TYPE: DNA
<213> ORGANISM: Homo sapiens

<400> SEQUENCE: 1
atgagtgctg aggggtacca gtacagagcg ctgtatgatt ataaaaagga aagagaagaa      60
gatattgact tgcacttggg tgacatattg actgtgaata aagggtcctt agtagctctt     120
ggattcagtg atggacagga agccaggcct gaagaaattg gctggttaaa tggctataat     180
gaaaccacag gggaaagggg ggactttccg ggaacttacg tagaatatat tggaaggaaa     240
aaaatctcgc ctcccacacc aaagcccgg ccacctcggc ctcttcctgt tgcaccaggt      300
tcttcgaaaa ctgaagcaga tgttgaacaa caagctttga ctctcccgga tcttgcagag     360
cagtttgccc ctcctgacat tgccccgcct cttcttatca agctcgtgga agccattgaa     420
aagaaaggtc tggaatgttc aactctatac agaacacaga gctccagcaa cctggcagaa     480
ttacgacagc ttcttgattg tgatacaccc tccgtggact tggaaatgat cgatgtgcac     540
gttttggctg acgctttcaa acgctatctc ctggacttac caaatcctgt cattccagca     600
gccgtttaca gtgaaatgat ttctttagct ccagaagtac aaagctccga agaatatatt     660
```

```
cagctattga agaagcttat taggtcgcct agcatacctc atcagtattg gcttacgctt    720
cagtatttgt taaacatttt cttcaagctc tctcaaacct ccagcaaaaa tctgttgaat    780
gcaagagtac tctctgaaat tttcagccct atgcttttca gattctcagc agccagctct    840
gataatactg aaaacctcat aaaagttata gaaattttaa tctcaactga atggaatgaa    900
cgacagcctg caccagcact gcctcctaaa ccaccaaaac ctactactgt agccaacaac    960
ggtatgaata acaatatgtc cttacaagat gctgaatggt actggggaga tatctcgagg   1020
gaagaagtga atgaaaaact tcgagataca gcagacggga cctttttggt acgagatgcg   1080
tctactaaaa tgcatggtga ttatactctt acactaagga aaggggaaa taacaaatta    1140
atcaaaatat ttcatcgaga tgggaaatat ggcttctctg acccattaac cttcagttct   1200
gtggttgaat taataaacca ctaccggaat gaatctctag ctcagtataa tcccaaattg   1260
gatgtgaaat tactttatcc agtatccaaa taccaacagg atcaagttgt caaagaagat   1320
aatattgaag ctgtagggaa aaaattacat gaatataaca ctcagtttca agaaaaaagt   1380
cgagaatatg atagattata tgaagaatat acccgcacat cccaggaaat ccaaatgaaa   1440
aggacagcta ttgaagcatt taatgaaacc ataaaaatat ttgaagaaca gtgccagacc   1500
caagagcggt acagcaaaga atacatagaa aagtttaaac gtgaaggcaa tgagaaagaa   1560
atacaaagga ttatgcataa ttatgataag ttgaagtctc gaatcagtga aattattgac   1620
agtagaagaa gattggaaga agacttgaag aagcaggcag ctgagtatcg agaaattgac   1680
aaacgtatga acagcattaa accagacctt atccagctga aaagacgag agaccaatac     1740
ttgatgtggt tgactcaaaa aggtgttcgg caaaagaagt tgaacgagtg gttgggcaat   1800
gaaaacactg aagaccaata ttcactggtg gaagatgatg aagatttgcc ccatcatgat   1860
gagaagacat ggaatgttgg aagcagcaac cgaaacaaag ctgaaaacct gttgcgaggg   1920
aagcgagatg gcacttttct tgtccgggag agcagtaaac agggctgcta tgcctgctct   1980
gtagtggtgg acggcgaagt aaagcattgt gtcataaaca aacagcaac tggctatggc     2040
tttgccgagc cctataactt gtacagctct ctga                                2074

<210> SEQ ID NO 2
<211> LENGTH: 724
<212> TYPE: PRT
<213> ORGANISM: Homo sapiens

<400> SEQUENCE: 2

Met Ser Ala Glu Gly Tyr Gln Tyr Arg Ala Leu Tyr Asp Tyr Lys Lys
1               5                   10                  15

Glu Arg Glu Glu Asp Ile Asp Leu His Leu Gly Asp Ile Leu Thr Val
            20                  25                  30

Asn Lys Gly Ser Leu Val Ala Leu Gly Phe Ser Asp Gly Gln Glu Ala
        35                  40                  45

Arg Pro Glu Glu Ile Gly Trp Leu Asn Gly Tyr Asn Glu Thr Thr Gly
    50                  55                  60

Glu Arg Gly Asp Phe Pro Gly Thr Tyr Val Glu Tyr Ile Gly Arg Lys
65                  70                  75                  80

Lys Ile Ser Pro Pro Thr Pro Lys Pro Arg Pro Pro Arg Pro Leu Pro
                85                  90                  95

Val Ala Pro Gly Ser Ser Lys Thr Glu Ala Asp Val Glu Gln Gln Ala
            100                 105                 110

Leu Thr Leu Pro Asp Leu Ala Glu Gln Phe Ala Pro Pro Asp Ile Ala
        115                 120                 125
```

```
Pro Pro Leu Leu Ile Lys Leu Val Glu Ala Ile Glu Lys Lys Gly Leu
    130                 135                 140

Glu Cys Ser Thr Leu Tyr Arg Thr Gln Ser Ser Asn Leu Ala Glu
145                 150                 155                 160

Leu Arg Gln Leu Leu Asp Cys Asp Thr Pro Ser Val Asp Leu Glu Met
                    165                 170                 175

Ile Asp Val His Val Leu Ala Asp Ala Phe Lys Arg Tyr Leu Leu Asp
                180                 185                 190

Leu Pro Asn Pro Val Ile Pro Ala Ala Val Tyr Ser Glu Met Ile Ser
            195                 200                 205

Leu Ala Pro Glu Val Gln Ser Ser Glu Glu Tyr Ile Gln Leu Leu Lys
        210                 215                 220

Lys Leu Ile Arg Ser Pro Ser Ile Pro His Gln Tyr Trp Leu Thr Leu
225                 230                 235                 240

Gln Tyr Leu Leu Lys His Phe Phe Lys Leu Ser Gln Thr Ser Ser Lys
                    245                 250                 255

Asn Leu Leu Asn Ala Arg Val Leu Ser Glu Ile Phe Ser Pro Met Leu
                260                 265                 270

Phe Arg Phe Ser Ala Ala Ser Ser Asp Asn Thr Glu Asn Leu Ile Lys
            275                 280                 285

Val Ile Glu Ile Leu Ile Ser Thr Glu Trp Asn Glu Arg Gln Pro Ala
290                 295                 300

Pro Ala Leu Pro Pro Lys Pro Pro Lys Pro Thr Thr Val Ala Asn Asn
305                 310                 315                 320

Gly Met Asn Asn Asn Met Ser Leu Gln Asp Ala Glu Trp Tyr Trp Gly
                    325                 330                 335

Asp Ile Ser Arg Glu Glu Val Asn Glu Lys Leu Arg Asp Thr Ala Asp
                340                 345                 350

Gly Thr Phe Leu Val Arg Asp Ala Ser Thr Lys Met His Gly Asp Tyr
            355                 360                 365

Thr Leu Thr Leu Arg Lys Gly Gly Asn Asn Lys Leu Ile Lys Ile Phe
        370                 375                 380

His Arg Asp Gly Lys Tyr Gly Phe Ser Asp Pro Leu Thr Phe Ser Ser
385                 390                 395                 400

Val Val Glu Leu Ile Asn His Tyr Arg Asn Glu Ser Leu Ala Gln Tyr
                    405                 410                 415

Asn Pro Lys Leu Asp Val Lys Leu Leu Tyr Pro Val Ser Lys Tyr Gln
                420                 425                 430

Gln Asp Gln Val Val Lys Glu Asp Asn Ile Glu Ala Val Gly Lys Lys
            435                 440                 445

Leu His Glu Tyr Asn Thr Gln Phe Gln Glu Lys Ser Arg Glu Tyr Asp
        450                 455                 460

Arg Leu Tyr Glu Glu Tyr Thr Arg Thr Ser Gln Glu Ile Gln Met Lys
465                 470                 475                 480

Arg Thr Ala Ile Glu Ala Phe Asn Glu Thr Ile Lys Ile Phe Glu Glu
                    485                 490                 495

Gln Cys Gln Thr Gln Glu Arg Tyr Ser Lys Glu Tyr Ile Glu Lys Phe
                500                 505                 510

Lys Arg Glu Gly Asn Glu Lys Glu Ile Gln Arg Ile Met His Asn Tyr
            515                 520                 525

Asp Lys Leu Lys Ser Arg Ile Ser Glu Ile Ile Asp Ser Arg Arg Arg
        530                 535                 540

Leu Glu Glu Asp Leu Lys Lys Gln Ala Ala Glu Tyr Arg Glu Ile Asp
```

```
                   545                 550                 555                 560
Lys Arg Met Asn Ser Ile Lys Pro Asp Leu Ile Gln Leu Arg Lys Thr
                565                 570                 575

Arg Asp Gln Tyr Leu Met Trp Leu Thr Gln Lys Gly Val Arg Gln Lys
                580                 585                 590

Lys Leu Asn Glu Trp Leu Gly Asn Glu Asn Thr Glu Asp Gln Tyr Ser
                595                 600                 605

Leu Val Glu Asp Asp Glu Asp Leu Pro His His Asp Glu Lys Thr Trp
            610                 615                 620

Asn Val Gly Ser Ser Asn Arg Asn Lys Ala Glu Asn Leu Leu Arg Gly
625                 630                 635                 640

Lys Arg Asp Gly Thr Phe Leu Val Arg Glu Ser Ser Lys Gln Gly Cys
                645                 650                 655

Tyr Ala Cys Ser Val Val Val Asp Gly Glu Val Lys His Cys Val Ile
                660                 665                 670

Asn Lys Thr Ala Thr Gly Tyr Gly Phe Ala Glu Pro Tyr Asn Leu Tyr
                675                 680                 685

Ser Ser Leu Lys Glu Leu Val Leu His Tyr Gln His Thr Ser Leu Val
                690                 695                 700

Gln His Asn Asp Ser Leu Asn Val Thr Leu Ala Tyr Pro Val Tyr Ala
705                 710                 715                 720

Gln Gln Arg Arg

<210> SEQ ID NO 3
<211> LENGTH: 6453
<212> TYPE: DNA
<213> ORGANISM: Homo sapiens

<400> SEQUENCE: 3
tacaaccagg ctcaactgtt gcatggtagc agatttgcaa acatgagtgc tgagggtac        60
cagtacagag cgctgtatga ttataaaaag gaaagagaag aagatattga cttgcacttg      120
ggtgacatat tgactgtgaa taagggtccc ttagtagctc ttggattcag tgatggacag      180
gaagccaggc ctgaagaaat tggctggtta atggctata atgaaccac aggggaaagg        240
ggggactttc cgggaactta cgtagaatat attggaagga aaaaaatctc gcctcccaca      300
ccaaagcccc ggccacctcg gcctcttcct gttgcaccag ttcttcgaa aactgaagca       360
gatgttgaac aacaagcttt gactctcccg gatcttgcag agcagtttgc ccctcctgac      420
attgccccgc tcttcttat caagctcgtg gaagccattg aaaagaaagg tctggaatgt       480
tcaactctat acagaacaca gagctccagc aacctggcag aattacgaca gcttcttgat      540
tgtgatacac cctccgtgga cttggaaatg atcgatgtgc acgttttggc tgacgctttc      600
aaacgctatc tcctggactt accaaatcct gtcattccag cagccgttta cagtgaaatg      660
atttctttag ctccagaagt acaaagctcc gaagaatata ttcagctatt gaagaagctt      720
attaggtcgc ctagcatacc tcatcagtat tggcttacgc ttcagtattt gttaaaacat      780
ttcttcaagc tctctcaaac ctccagcaaa atctgttga atgcaagagt actctctgaa       840
attttcagcc ctatgctttt cagattctca gcagccagct ctgataatac tgaaaacctc      900
ataaaagtta tagaaatttt aatctcaact gaatggaatg aacgacagcc tgcaccagca      960
ctgcctccta accaccaaa acctactact gtagccaaca acggtatgaa taacaatatg     1020
tccttacaag atgctgaatg gtactgggga gatatctcga gggaagaagt gaatgaaaaa     1080
cttcgagata cagcagacgg gacctttttg gtacgagatg cgtctactaa aatgcatggt     1140
```

```
gattatactc ttacactaag gaaaggggga aataacaaat taatcaaaat atttcatcga    1200
gatgggaaat atggcttctc tgacccatta accttcagtt ctgtggttga attaataaac    1260
cactaccgga atgaatctct agctcagtat aatcccaaat tggatgtgaa attactttat    1320
ccagtatcca aataccaaca ggatcaagtt gtcaaagaag ataatattga agctgtaggg    1380
aaaaaattac atgaatataa cactcagttt caagaaaaaa gtcgagaata tgatagatta    1440
tatgaagaat atacccgcac atcccaggaa atccaaatga aaaggacagc tattgaagca    1500
tttaatgaaa ccataaaaat atttgaagaa cagtgccaga cccaagagcg gtacagcaaa    1560
gaatacatag aaaagtttaa acgtgaaggc aatgagaaag aaatacaaag gattatgcat    1620
aattatgata agttgaagtc tcgaatcagt gaaattattg acagtagaag aagattggaa    1680
gaagacttga agaagcaggc agctgagtat cgagaaattg acaaacgtat gaacagcatt    1740
aaaccagacc ttatccagct gagaaagacg agagaccaat acttgatgtg gttgactcaa    1800
aaaggtgttc ggcaaaagaa gttgaacgag tggttgggca atgaaaacac tgaagaccaa    1860
tattcactgg tggaagatga tgaagatttg ccccatcatg atgagaagac atggaatgtt    1920
ggaagcagca accgaaacaa agctgaaaac ctgttgcgag ggaagcgaga tggcactttt    1980
cttgtccggg agagcagtaa acagggctgc tatgcctgct ctgtagtggt ggacggcgaa    2040
gtaaagcatt gtgtcataaa caaaacagca actggctatg gctttgccga gccctataac    2100
ttgtacagct ctctgaaaga actggtgcta cattaccaac acacctccct tgtgcagcac    2160
aacgactccc tcaatgtcac actagcctac ccagtatatg cacagcagag gcgatgaagc    2220
gcttactctt tgatccttct cctgaagttc agccaccctg aggcctctgg aaagcaaagg    2280
gctcctctcc agtctgatct gtgaattgag ctgcagaaac gaagccatct ttctttggat    2340
gggactagag cttctttca caaaaagaa gtaggggaag acatgcagcc taaggctgta    2400
tgatgaccac acgttcctaa gctggagtgc ttatcccttc ttttctttt tttctttggt    2460 ttaatttaaa gccacaacca catacaacac aaagagaaaa agaaatgcaa aaatctctgc    2520
gtgcagggac aaagaggcct ttaaccatgg tgcttgttaa tgctttctga agctttacca    2580
gctgaaagtt gggactctgg agagcggagg agagagaggc agaagaaccc tggcctgaga    2640
aggtttggtc cagcctggtt tagcctggat gttgctgtgc acggtggacc cagacacatc    2700
gcactgtgga ttatttcatt ttgtaacaaa tgaacgatat gtagcagaaa ggcacgtcca    2760
ctcacaaggg acgctttggg agaatgtcag ttcatgtatg ttcagaagaa attctgtcat    2820
agaaagtgcc agaaagtgtt taacttgtca aaaaacaaaa acccagcaac agaaaaatgg    2880
agtttggaaa acaggactta aaatgacatt cagtatataa aatatgtaca taatattgga    2940
tgactaacta tcaaatagat ggatttgtat caataccaaa tagcttctgt tttgttttgc    3000
tgaaggctaa attcacagcg ctatgcaatt cttaattttc attaagttgt tatttcagtt    3060
ttaaatgtac cttcagaata agcttcccca ccccagtttt tgttgcttga aaatattgtt    3120
gtcccggatt tttgttaata ttcatttttg ttatccttt taaaagtaa atgtacagga    3180 tgccagtaaa aaaaaaaaat ggcttcagaa ttaaaactat gaaatatttt acagtttttc    3240
ttgtacagag tacttggctg ttagcccaag gttaaaaagt tcataacaga ttttttttgg    3300
actgttttgt tgggcagtgc ctgataagct tcaaagctgc tttattcaat aaaaaaaaga    3360
aatgaaaaag atatatgaat atgacaaagt attgctgagt ccaacaatgt tgttttaaga    3420
ctcttaaaat acggtacctg gcaatgttta tttcataaag aattgtgaac ttcttgaatc    3480
tagggagggg gaatgtagtg aagggatgta tcaagtgggg tggtgggagg gggaggcaag    3540
```

```
gttatatgca ctttctcatg atttacagag aagtgaataa ctgcaaagtg aagttgcttc   3600
ttctacttca gtcttctctc actttgattt gctagttgtt atcaattaat gacaattaca   3660
aacctactgt atctctaata cagtgtgact ggtcaggtat ttcagttctt aggaaggaag   3720
tgccaagttt gtttttgggt tcctggaaca gcgctcacct tgtttagaa cactggttta    3780 aagggataat catctctgtc acattagact atccatcatg accagcaaat actcatttta   3840
ggaaaaaaaa aagcatgatc tgaaaaatac ttttggtggt atgttggtta ccctcctagc   3900
tttccatttg gtttagaaca taaagcaaat agacacagtc atactgtcac tgctctggac   3960
tgtgtggagc tcgctaaagt catggtcatt gcaggaatcc aagtggcagt ccttctcatt   4020
cattctaatc attgtatgtg cttcactacg ggggggagaa ggaaacgtta gcatcatgtt   4080
tcccatttag ggcaggagtg agaggtctct cttcctgatt tagatatgca aaagctggta   4140
tgttcagtag gaactgtaca tgtgttggga ggcataaaga ctaattagca accataatat   4200
ggtcactacc ctaatagact aaatgaaatc ttgcaatttc aaattactct ttctccatat   4260
tagatttacc cacagctata tttctgttta agtactaggg tgagggtttt ctgttacttt   4320
gttttttaat gttgttcctt tgaaagaat cagtcttgca gctgagtgaa aaatctgtgg    4380
aatgtattat ttgtcctctt tacatgaaac tactcatact taagcaaaag tcagtcttat   4440
agcaagactg ttagccctca aacttgactc tactgatctg accatttccc tctcatcgcc   4500
agacaactga cgatttccct ggttttagtc tgcgtctctg ctttaaagtt attgtgatat   4560
ccttctagat catacacaag tctaacagtt aattagttaa cagttttta actaggtttg    4620 tgggtatttt tttggtagca catgtatgct attacataca aattttt att tctaaaatat   4680 aagatctgag attgaatatt ttcattaaaa gctacagttt tgtgaatctt tgtgcttcaa   4740
cattctttgc aagatgatac ggtatttagg catttgcctt attttttgcat ctcacaaaca   4800 taagtgcaat agatcttttc attgaacagc aaagtaggat tcatcattcc atatgacttg   4860
agttacacca gacctgttct gcccaatgcc ttttgatta cagtgtagct tgcccaccgc    4920
atttgtcgtt ttagatactt tgctagccgg ccactttgga tttcatcaga cagtcctaac   4980
aatattgtct gaacggctga atatgaatag atacagcaga ggcactcctg atatatgatt   5040
tttatccatg cgtcagtttt tcccacccag tgtagcatcc taaagataaa gccagaagct   5100
aagctgcagt gaggctgtga ttgggcgtag aagtgggagc attgggacct cacattacac   5160
acacgagaga tcataaccat gtgaaaaggc aaaaagcatg tgtttgcaac atctgataac   5220
ttcatggcct tgataaatg tatatatgta tatgtgcatg gactgtgttt ccagtacacc     5280
tttcagccaa acagatcca cagtagttgt tgagttcaag tacataaagt acataacaag    5340
cgaacgtcta gtacaattct tacttatgtg tatgggattt tcccctttga ggttgctttg   5400
ttttgtctta caaaggtgaa aattgtttgt aagtgaagtg agaagttcat atttctttgg   5460
cttttttgtg tttttaaaag ttactccttt tagggagctg gtctgatgac ttgcttagct   5520
tggaaatcct tgttttcagt gtgtcgagtc aaaatgtgtt tatgtgagct gtcactgtgg   5580
ggaaccaatt gctttgtcat atagctggtt atgaactagt aacatgtttg ggaagtccta   5640
ctgatgttcc tttggaagaa aaaatctgct ggttttaaca actgtgcttt tgctatgtat   5700
ggtatccaag ttagttgaaa cgcagacact gagatctgtt tgagtttagg gtcattttta   5760
gaaaggggca gtttaaagca caatgtctca catgggacaa agttccaaaa tgccaaattc   5820
ttatttttta aaaagctagt tctataaaat actggtatta tgggtgggga ggaaatagaa   5880
ttgagtcaat tggaaagact atccaactta acatgaaact tgtcaccatg agatagcatt   5940
```

-continued

```
agctgcccag gatgctgcta tatatatata tatatatata tatgtgtgtg tgtgtgtgtg   6000
tgtgtgtgta tatatatata tatatatata tatatatata tatatatatg tgtgtgtata   6060
tatatatata tgtgtatata tatatgtata tacatatatg tatatatatg cacatatata   6120
tatgtattta aaaaaatcaa aacaaaaaaa aactcattta tacctgtgta tttttttaaag  6180 ctacaatctg ttcaatgttt ttaaaaatct gtttatatga cattgttaaa ataaagttgg   6240
tcttttgacg agagggagga tgtcacggtc agttgtaact ttgccttcac aaggcaactg   6300 gggtggggg tgggggtagt gtgcctcctt gacatttcgt tcaagttata gattcaatgg    6360
agctatgtct tgttttaagt tgctttaatg cattgtatta gatcttcaaa cagaataaag   6420
gttgttttga aactgaaaaa aaaaaaaaaa aaa                                 6453
```

<210> SEQ ID NO 4
<211> LENGTH: 454
<212> TYPE: PRT
<213> ORGANISM: Homo sapiens

<400> SEQUENCE: 4

```
Met Tyr Asn Thr Val Trp Asn Met Glu Asp Leu Asp Leu Glu Tyr Ala
1               5                   10                  15

Lys Thr Asp Ile Asn Cys Gly Thr Asp Leu Met Phe Tyr Ile Glu Met
            20                  25                  30

Asp Pro Pro Ala Leu Pro Pro Lys Pro Lys Pro Thr Thr Val Ala
        35                  40                  45

Asn Asn Gly Met Asn Asn Met Ser Leu Gln Asp Ala Glu Trp Tyr
    50                  55                  60

Trp Gly Asp Ile Ser Arg Glu Glu Val Asn Glu Lys Leu Arg Asp Thr
65                  70                  75                  80

Ala Asp Gly Thr Phe Leu Val Arg Asp Ala Ser Thr Lys Met His Gly
                85                  90                  95

Asp Tyr Thr Leu Thr Leu Arg Lys Gly Gly Asn Asn Lys Leu Ile Lys
            100                 105                 110

Ile Phe His Arg Asp Gly Lys Tyr Gly Phe Ser Asp Pro Leu Thr Phe
        115                 120                 125

Ser Ser Val Val Glu Leu Ile Asn His Tyr Arg Asn Glu Ser Leu Ala
    130                 135                 140

Gln Tyr Asn Pro Lys Leu Asp Val Lys Leu Leu Tyr Pro Val Ser Lys
145                 150                 155                 160

Tyr Gln Gln Asp Gln Val Val Lys Glu Asp Asn Ile Glu Ala Val Gly
                165                 170                 175

Lys Lys Leu His Glu Tyr Asn Thr Gln Phe Gln Glu Lys Ser Arg Glu
            180                 185                 190

Tyr Asp Arg Leu Tyr Glu Glu Tyr Thr Arg Thr Ser Gln Glu Ile Gln
        195                 200                 205

Met Lys Arg Thr Ala Ile Glu Ala Phe Asn Glu Thr Ile Lys Ile Phe
    210                 215                 220

Glu Glu Gln Cys Gln Thr Gln Glu Arg Tyr Ser Lys Glu Tyr Ile Glu
225                 230                 235                 240

Lys Phe Lys Arg Glu Gly Asn Glu Lys Glu Ile Gln Arg Ile Met His
                245                 250                 255

Asn Tyr Asp Lys Leu Lys Ser Arg Ile Ser Glu Ile Ile Asp Ser Arg
            260                 265                 270

Arg Arg Leu Glu Glu Asp Leu Lys Lys Gln Ala Ala Glu Tyr Arg Glu
        275                 280                 285
```

```
Ile Asp Lys Arg Met Asn Ser Ile Lys Pro Asp Leu Ile Gln Leu Arg
        290                 295                 300

Lys Thr Arg Asp Gln Tyr Leu Met Trp Leu Thr Gln Lys Gly Val Arg
305                 310                 315                 320

Gln Lys Lys Leu Asn Glu Trp Leu Gly Asn Glu Asn Thr Glu Asp Gln
                325                 330                 335

Tyr Ser Leu Val Glu Asp Glu Asp Leu Pro His His Asp Glu Lys
                340                 345                 350

Thr Trp Asn Val Gly Ser Ser Asn Arg Asn Lys Ala Glu Asn Leu Leu
            355                 360                 365

Arg Gly Lys Arg Asp Gly Thr Phe Leu Val Arg Glu Ser Ser Lys Gln
    370                 375                 380

Gly Cys Tyr Ala Cys Ser Val Val Asp Gly Glu Val Lys His Cys
385                 390                 395                 400

Val Ile Asn Lys Thr Ala Thr Gly Tyr Gly Phe Ala Glu Pro Tyr Asn
                405                 410                 415

Leu Tyr Ser Ser Leu Lys Glu Leu Val Leu His Tyr Gln His Thr Ser
                420                 425                 430

Leu Val Gln His Asn Asp Ser Leu Asn Val Thr Leu Ala Tyr Pro Val
            435                 440                 445

Tyr Ala Gln Gln Arg Arg
    450

<210> SEQ ID NO 5
<211> LENGTH: 424
<212> TYPE: PRT
<213> ORGANISM: Homo sapiens

<400> SEQUENCE: 5

Met His Asn Leu Gln Thr Leu Pro Pro Lys Pro Pro Lys Pro Thr Thr
1               5                   10                  15

Val Ala Asn Asn Gly Met Asn Asn Met Ser Leu Gln Asp Ala Glu
                20                  25                  30

Trp Tyr Trp Gly Asp Ile Ser Arg Glu Glu Val Asn Glu Lys Leu Arg
            35                  40                  45

Asp Thr Ala Asp Gly Thr Phe Leu Val Arg Asp Ala Ser Thr Lys Met
    50                  55                  60

His Gly Asp Tyr Thr Leu Thr Leu Arg Lys Gly Gly Asn Asn Lys Leu
65                  70                  75                  80

Ile Lys Ile Phe His Arg Asp Gly Lys Tyr Gly Phe Ser Asp Pro Leu
                85                  90                  95

Thr Phe Ser Ser Val Val Glu Leu Ile Asn His Tyr Arg Asn Glu Ser
                100                 105                 110

Leu Ala Gln Tyr Asn Pro Lys Leu Asp Val Lys Leu Leu Tyr Pro Val
            115                 120                 125

Ser Lys Tyr Gln Gln Asp Gln Val Val Lys Glu Asp Asn Ile Glu Ala
    130                 135                 140

Val Gly Lys Lys Leu His Glu Tyr Asn Thr Gln Phe Gln Glu Lys Ser
145                 150                 155                 160

Arg Glu Tyr Asp Arg Leu Tyr Glu Glu Tyr Thr Arg Thr Ser Gln Glu
                165                 170                 175

Ile Gln Met Lys Arg Thr Ala Ile Glu Ala Phe Asn Glu Thr Ile Lys
            180                 185                 190

Ile Phe Glu Glu Gln Cys Gln Thr Gln Glu Arg Tyr Ser Lys Glu Tyr
        195                 200                 205
```

```
Ile Glu Lys Phe Lys Arg Glu Gly Asn Glu Lys Glu Ile Gln Arg Ile
210                 215                 220

Met His Asn Tyr Asp Lys Leu Lys Ser Arg Ile Ser Glu Ile Ile Asp
225                 230                 235                 240

Ser Arg Arg Arg Leu Glu Glu Asp Leu Lys Lys Gln Ala Ala Glu Tyr
                245                 250                 255

Arg Glu Ile Asp Lys Arg Met Asn Ser Ile Lys Pro Asp Leu Ile Gln
                260                 265                 270

Leu Arg Lys Thr Arg Asp Gln Tyr Leu Met Trp Leu Thr Gln Lys Gly
        275                 280                 285

Val Arg Gln Lys Lys Leu Asn Glu Trp Leu Gly Asn Glu Asn Thr Glu
290                 295                 300

Asp Gln Tyr Ser Leu Val Glu Asp Asp Glu Asp Leu Pro His His Asp
305                 310                 315                 320

Glu Lys Thr Trp Asn Val Gly Ser Ser Asn Arg Asn Lys Ala Glu Asn
                325                 330                 335

Leu Leu Arg Gly Lys Arg Asp Gly Thr Phe Leu Val Arg Glu Ser Ser
                340                 345                 350

Lys Gln Gly Cys Tyr Ala Cys Ser Val Val Val Asp Gly Glu Val Lys
        355                 360                 365

His Cys Val Ile Asn Lys Thr Ala Thr Gly Tyr Gly Phe Ala Glu Pro
370                 375                 380

Tyr Asn Leu Tyr Ser Ser Leu Lys Glu Leu Val Leu His Tyr Gln His
385                 390                 395                 400

Thr Ser Leu Val Gln His Asn Asp Ser Leu Asn Val Thr Leu Ala Tyr
                405                 410                 415

Pro Val Tyr Ala Gln Gln Arg Arg
            420

<210> SEQ ID NO 6
<211> LENGTH: 3207
<212> TYPE: DNA
<213> ORGANISM: Homo sapiens

<400> SEQUENCE: 6
atgcctccac gaccatcatc aggtgaactg tggggcatcc acttgatgcc cccaagaatc      60
ctagtagaat gtttactacc aaatggaatg atagtgactt tagaatgcct ccgtgaggct     120
acattaataa ccataaagca tgaactattt aaagaagcaa gaaaataccc cctccatcaa     180
cttcttcaag atgaatcttc ttacattttc gtaagtgtta ctcaagaagc agaaagggaa     240
gaattttttg atgaaacaag acgactttgt gaccttcggc ttttccaacc cttttttaaa     300
gtaattgaac cagtaggcaa ccgtgaagaa agatcctca atcgagaaat ggttttgct      360 atcggcatgc cagtgtgtga atttgatatg gttaaagatc cagaagtaca ggacttccga     420
agaaatattc tgaacgtttg taagaagct gtggatctta gggaccctca ttcacctcat      480
agtagagcaa tgtatgtcta tcctccaaat gtagaatctt caccagaatt gccaaagcac     540
atatataata aattagataa agggcaaata atagtggtga tctgggtaat agtttctcca     600
aataatgaca agcagaagta tactctgaaa atcaaccatg actgtgtacc agaacaagta     660
attgctgaag caatcaggaa aaaaactcga agtatgttgc tatcctctga caactaaaa      720 ctctgtgttt tagaatatca gggcaagtat attttaaaag tgtgtggatg tgatgaatac     780
ttcctagaaa aatatcctct gagtcagtat aagtatataa aagctgtat aatgcttggg     840 aggatgccca atttgatgtt gatggctaaa gaaagccttt attctcaact gccaatggac     900
```

```
tgttttacaa tgccatctta ttccagacgc atttccacag ctacaccata tatgaatgga    960
gaaacatcta caaaatccct tgggttata aatagtgcac tcagaataaa aattctttgt   1020
gcaacctacg tgaatgtaaa tattcgagac attgataaga tctatgttcg aacaggtatc  1080
taccatggag gagaacccttt atgtgacaat gtgaacactc aaagagtacc ttgttccaat 1140
cccaggtgga atgaatggct gaattatgat atatacattc ctgatcttcc tcgtgctgct  1200
cgactttgcc tttccatttg ctctgttaaa ggccgaaagg gtgctaaaga ggaacactgt  1260
ccattggcat ggggaaatat aaacttgttt gattacacag acactctagt atctggaaaa 1320
atggctttga tctttggcc agtacctcat ggattagaag atttgctgaa ccctattggt   1380
gttactggat caaatccaaa taaagaaact ccatgcttag agttggagtt tgactggttc  1440
agcagtgtgg taaagttccc agatatgtca gtgattgaag agcatgccaa ttggtctgta  1500
tcccgagaag caggatttag ctattcccac gcaggactga gtaacagact agctagagac 1560
aatgaattaa gggaaaatga caagaacag ctcaaagcaa tttctacacg agatcctctc   1620
tctgaaatca ctgagcagga gaaagatttt ctatggagtc acagacacta ttgtgtaact 1680
atccccgaaa ttctacccaa attgcttctg tctgttaaat ggaattctag agatgaagta 1740
gcccagatgt attgcttggt aaaagattgg cctccaatca aacctgaaca ggctatggaa 1800
cttctggact gtaattaccc agatcctatg gttcgaggtt ttgctgttcg gtgcttggaa 1860
aaatatttaa cagatgacaa actttctcag tatttaattc agctagtaca ggtcctaaaa 1920
tatgaacaat atttggataa cttgcttgtg agattttac tgaagaaagc attgactaat   1980
caaaggattg ggcactttt cttttggcat ttaaaatctg agatgcacaa taaaacagtt   2040
agccagaggt ttggcctgct tttgagtcc tattgtcgtg catgtgggat gtatttgaag   2100
cacctgaata ggcaagtcga ggcaatggaa aagctcatta acttaactga cattctcaaa 2160
caggagaaga aggatgaaac acaaaaggta cagatgaagt ttttagttga gcaaatgagg 2220
cgaccagatt tcatggatgc tctacagggc tttctgtctc ctctaaaccc tgctcatcaa 2280
ctaggaaaacc tcaggcttga agagtgtcga attatgtcct ctgcaaaaag gccactgtgg 2340
ttgaattggg agaacccaga catcatgtca gagttactgt ttcagaacaa tgagatcatc 2400
tttaaaaatg gggatgattt acggcaagat atgctaacac ttcaaattat tcgtattatg 2460
gaaaatatct ggcaaaatca aggtcttgat cttcgaatgt taccttatgg ttgtctgtca 2520
atcggtgact gtgtgggact tattgaggtg gtgcgaaatt ctcacactat tatgcaaatt  2580
cagtgcaaag gcggcttgaa aggtgcactg cagttcaaca gccacacact acatcagtgg 2640
ctcaaagaca agaacaaagg agaaatatat gatgcagcca ttgacctgtt tacacgttca  2700
tgtgctggat actgtgtagc taccttcatt ttgggaattg gagatcgtca caatagtaac 2760
atcatggtga aagacgatgg acaactgttt catatagatt ttggacactt tttggatcac 2820
aagaagaaaa aatttggtta taaacgagaa cgtgtgccat tgttttgac acaggatttc   2880
ttaatagtga ttagtaaagg agcccaagaa tgcacaaaga caagagaatt tgagaggttt  2940
caggagatgt gttacaaggc ttatctagct attcgacagc atgccaatct cttcataaat  3000
ctttctcaa tgatgcttgg ctctggaatg ccagaactac aatcttttga tgacattgca  3060
tacattcgaa agaccctagc cttagataaa actgagcaag aggctttgga gtatttcatg 3120
aaacaaatga atgatgcaca tcatggtggc tggacaacaa aaatggattg gatcttccac 3180
acaattaaac agcatgcatt gaactga                                     3207

<210> SEQ ID NO 7
```

<211> LENGTH: 1068
<212> TYPE: PRT
<213> ORGANISM: Homo sapiens

<400> SEQUENCE: 7

```
Met Pro Pro Arg Pro Ser Ser Gly Glu Leu Trp Gly Ile His Leu Met
1               5                   10                  15

Pro Pro Arg Ile Leu Val Glu Cys Leu Leu Pro Asn Gly Met Ile Val
            20                  25                  30

Thr Leu Glu Cys Leu Arg Glu Ala Thr Leu Ile Thr Ile Lys His Glu
        35                  40                  45

Leu Phe Lys Glu Ala Arg Lys Tyr Pro Leu His Gln Leu Leu Gln Asp
    50                  55                  60

Glu Ser Ser Tyr Ile Phe Val Ser Val Thr Gln Glu Ala Glu Arg Glu
65                  70                  75                  80

Glu Phe Phe Asp Glu Thr Arg Arg Leu Cys Asp Leu Arg Leu Phe Gln
                85                  90                  95

Pro Phe Leu Lys Val Ile Glu Pro Val Gly Asn Arg Glu Glu Lys Ile
            100                 105                 110

Leu Asn Arg Glu Ile Gly Phe Ala Ile Gly Met Pro Val Cys Glu Phe
        115                 120                 125

Asp Met Val Lys Asp Pro Glu Val Gln Asp Phe Arg Arg Asn Ile Leu
130                 135                 140

Asn Val Cys Lys Glu Ala Val Asp Leu Arg Asp Leu Asn Ser Pro His
145                 150                 155                 160

Ser Arg Ala Met Tyr Val Tyr Pro Pro Asn Val Glu Ser Ser Pro Glu
                165                 170                 175

Leu Pro Lys His Ile Tyr Asn Lys Leu Asp Lys Gly Gln Ile Ile Val
            180                 185                 190

Val Ile Trp Val Ile Val Ser Pro Asn Asn Asp Lys Gln Lys Tyr Thr
        195                 200                 205

Leu Lys Ile Asn His Asp Cys Val Pro Glu Gln Val Ile Ala Glu Ala
    210                 215                 220

Ile Arg Lys Lys Thr Arg Ser Met Leu Leu Ser Ser Glu Gln Leu Lys
225                 230                 235                 240

Leu Cys Val Leu Glu Tyr Gln Gly Lys Tyr Ile Leu Lys Val Cys Gly
                245                 250                 255

Cys Asp Glu Tyr Phe Leu Glu Lys Tyr Pro Leu Ser Gln Tyr Lys Tyr
            260                 265                 270

Ile Arg Ser Cys Ile Met Leu Gly Arg Met Pro Asn Leu Met Leu Met
        275                 280                 285

Ala Lys Glu Ser Leu Tyr Ser Gln Leu Pro Met Asp Cys Phe Thr Met
    290                 295                 300

Pro Ser Tyr Ser Arg Arg Ile Ser Thr Ala Thr Pro Tyr Met Asn Gly
305                 310                 315                 320

Glu Thr Ser Thr Lys Ser Leu Trp Val Ile Asn Ser Ala Leu Arg Ile
                325                 330                 335

Lys Ile Leu Cys Ala Thr Tyr Val Asn Val Asn Ile Arg Asp Ile Asp
            340                 345                 350

Lys Ile Tyr Val Arg Thr Gly Ile Tyr His Gly Gly Glu Pro Leu Cys
        355                 360                 365

Asp Asn Val Asn Thr Gln Arg Val Pro Cys Ser Asn Pro Arg Trp Asn
    370                 375                 380

Glu Trp Leu Asn Tyr Asp Ile Tyr Ile Pro Asp Leu Pro Arg Ala Ala
385                 390                 395                 400
```

-continued

```
Arg Leu Cys Leu Ser Ile Cys Ser Val Lys Gly Arg Lys Gly Ala Lys
            405                 410                 415
Glu Glu His Cys Pro Leu Ala Trp Gly Asn Ile Asn Leu Phe Asp Tyr
        420                 425                 430
Thr Asp Thr Leu Val Ser Gly Lys Met Ala Leu Asn Leu Trp Pro Val
            435                 440                 445
Pro His Gly Leu Glu Asp Leu Leu Asn Pro Ile Gly Val Thr Gly Ser
450                 455                 460
Asn Pro Asn Lys Glu Thr Pro Cys Leu Glu Leu Glu Phe Asp Trp Phe
465                 470                 475                 480
Ser Ser Val Val Lys Phe Pro Asp Met Ser Val Ile Glu Glu His Ala
                485                 490                 495
Asn Trp Ser Val Ser Arg Glu Ala Gly Phe Ser Tyr Ser His Ala Gly
            500                 505                 510
Leu Ser Asn Arg Leu Ala Arg Asp Asn Glu Leu Arg Glu Asn Asp Lys
        515                 520                 525
Glu Gln Leu Lys Ala Ile Ser Thr Arg Asp Pro Leu Ser Glu Ile Thr
    530                 535                 540
Glu Gln Glu Lys Asp Phe Leu Trp Ser His Arg His Tyr Cys Val Thr
545                 550                 555                 560
Ile Pro Glu Ile Leu Pro Lys Leu Leu Leu Ser Val Lys Trp Asn Ser
                565                 570                 575
Arg Asp Glu Val Ala Gln Met Tyr Cys Leu Val Lys Asp Trp Pro Pro
            580                 585                 590
Ile Lys Pro Glu Gln Ala Met Glu Leu Leu Asp Cys Asn Tyr Pro Asp
        595                 600                 605
Pro Met Val Arg Gly Phe Ala Val Arg Cys Leu Glu Lys Tyr Leu Thr
    610                 615                 620
Asp Asp Lys Leu Ser Gln Tyr Leu Ile Gln Leu Val Gln Val Leu Lys
625                 630                 635                 640
Tyr Glu Gln Tyr Leu Asp Asn Leu Leu Val Arg Phe Leu Leu Lys Lys
                645                 650                 655
Ala Leu Thr Asn Gln Arg Ile Gly His Phe Phe Phe Trp His Leu Lys
            660                 665                 670
Ser Glu Met His Asn Lys Thr Val Ser Gln Arg Phe Gly Leu Leu Leu
        675                 680                 685
Glu Ser Tyr Cys Arg Ala Cys Gly Met Tyr Leu Lys His Leu Asn Arg
    690                 695                 700
Gln Val Glu Ala Met Glu Lys Leu Ile Asn Leu Thr Asp Ile Leu Lys
705                 710                 715                 720
Gln Glu Lys Lys Asp Glu Thr Gln Lys Val Gln Met Lys Phe Leu Val
                725                 730                 735
Glu Gln Met Arg Arg Pro Asp Phe Met Asp Ala Leu Gln Gly Phe Leu
            740                 745                 750
Ser Pro Leu Asn Pro Ala His Gln Leu Gly Asn Leu Arg Leu Glu Glu
        755                 760                 765
Cys Arg Ile Met Ser Ser Ala Lys Arg Pro Leu Trp Leu Asn Trp Glu
    770                 775                 780
Asn Pro Asp Ile Met Ser Glu Leu Leu Phe Gln Asn Asn Glu Ile Ile
785                 790                 795                 800
Phe Lys Asn Gly Asp Asp Leu Arg Gln Asp Met Leu Thr Leu Gln Ile
                805                 810                 815
Ile Arg Ile Met Glu Asn Ile Trp Gln Asn Gln Gly Leu Asp Leu Arg
```

```
                    820             825                 830
Met Leu Pro Tyr Gly Cys Leu Ser Ile Gly Asp Cys Val Gly Leu Ile
            835                 840                 845

Glu Val Val Arg Asn Ser His Thr Ile Met Gln Ile Gln Cys Lys Gly
        850                 855                 860

Gly Leu Lys Gly Ala Leu Gln Phe Asn Ser His Thr Leu His Gln Trp
865                 870                 875                 880

Leu Lys Asp Lys Asn Lys Gly Glu Ile Tyr Asp Ala Ala Ile Asp Leu
                885                 890                 895

Phe Thr Arg Ser Cys Ala Gly Tyr Cys Val Ala Thr Phe Ile Leu Gly
            900                 905                 910

Ile Gly Asp Arg His Asn Ser Asn Ile Met Val Lys Asp Asp Gly Gln
        915                 920                 925

Leu Phe His Ile Asp Phe Gly His Phe Leu Asp His Lys Lys Lys Lys
    930                 935                 940

Phe Gly Tyr Lys Arg Glu Arg Val Pro Phe Val Leu Thr Gln Asp Phe
945                 950                 955                 960

Leu Ile Val Ile Ser Lys Gly Ala Gln Glu Cys Thr Lys Thr Arg Glu
                965                 970                 975

Phe Glu Arg Phe Gln Glu Met Cys Tyr Lys Ala Tyr Leu Ala Ile Arg
            980                 985                 990

Gln His Ala Asn Leu Phe Ile Asn Leu Phe Ser Met Met Leu Gly Ser
        995                 1000                1005

Gly Met Pro Glu Leu Gln Ser Phe Asp Asp Ile Ala Tyr Ile Arg
    1010                1015                1020

Lys Thr Leu Ala Leu Asp Lys Thr Glu Gln Glu Ala Leu Glu Tyr
    1025                1030                1035

Phe Met Lys Gln Met Asn Asp Ala His His Gly Gly Trp Thr Thr
    1040                1045                1050

Lys Met Asp Trp Ile Phe His Thr Ile Lys Gln His Ala Leu Asn
    1055                1060                1065

<210> SEQ ID NO 8
<211> LENGTH: 3724
<212> TYPE: DNA
<213> ORGANISM: Homo sapiens

<400> SEQUENCE: 8
tctccctcgg cgccgccgcc gccgcccgcg gggctgggac ccgatgcggt tagagccgcg      60
gagcctggaa gagccccgag cgtttctgct ttgggacaac catacatcta attccttaaa    120
gtagttttat atgtaaaact tgcaaagaat cagaacaatg cctccacgac catcatcagg    180
tgaactgtgg ggcatccact tgatgccccc aagaatccta gtagaatgtt tactaccaaa    240
tggaatgata gtgactttag aatgcctccg tgaggctaca ttaataacca taaagcatga    300
actatttaaa gaagcaagaa ataccccct ccatcaactt cttcaagatg aatcttctta    360
cattttcgta agtgttactc aagaagcaga aagggaagaa tttttgatg aaacaagacg    420 actttgtgac cttcggcttt ttcaacccct tttaaaagta attgaaccag taggcaaccg    480
tgaagaaaag atcctcaatc gagaaattgg ttttgctatc ggcatgccag tgtgtgaatt    540
tgatatggtt aaagatccag aagtacagga cttccgaaga atattctga cgtttgtaa    600 agaagctgtg gatcttaggg acctcaattc acctcatagt agagcaatgt atgtctatcc    660
tccaaatgta gaatcttcac cagaattgcc aaagcacata tataataaat tagataaagg    720
gcaaataata gtggtgatct gggtaatagt ttctccaaat aatgacaagc agaagtatac    780
```

```
tctgaaaatc aaccatgact gtgtaccaga acaagtaatt gctgaagcaa tcaggaaaaa    840
aactcgaagt atgttgctat cctctgaaca actaaaactc tgtgttttag aatatcaggg    900
caagtatatt ttaaaagtgt gtggatgtga tgaatacttc ctagaaaaat atcctctgag    960
tcagtataag tatataagaa gctgtataat gcttgggagg atgcccaatt tgatgttgat   1020
ggctaaagaa agcctttatt ctcaactgcc aatggactgt tttacaatgc catcttattc   1080
cagacgcatt tccacagcta caccatatat gaatggagaa acatctacaa aatccctttg   1140
ggttataaat agtgcactca gaataaaaat tctttgtgca acctacgtga atgtaaatat   1200
tcgagacatt gataagatct atgttcgaac aggtatctac catggaggag aacccttatg   1260
tgacaatgtg aacactcaaa gagtaccttg ttccaatccc aggtggaatg aatggctgaa   1320
ttatgatata tacattcctg atcttcctcg tgctgctcga ctttgccttt ccatttgctc   1380
tgttaaaggc cgaaagggtg ctaaagagga acactgtcca ttggcatggg gaaatataaa   1440
cttgtttgat tacacagaca ctctagtatc tggaaaaatg gctttgaatc tttggccagt   1500
acctcatgga ttagaagatt tgctgaaccc tattggtgtt actggatcaa atccaaataa   1560
agaaactcca tgcttagagt tggagtttga ctggttcagc agtgtggtaa agttcccaga   1620
tatgtcagtg attgaagagc atgccaattg gtctgtatcc cgagaagcag gatttagcta   1680
ttcccacgca ggactgagta acagactagc tagagacaat gaattaaggg aaaatgacaa   1740
agaacagctc aaagcaattt ctacacgaga tcctctctct gaaatcactg agcaggagaa   1800
agattttcta tggagtcaca gacactattg tgtaactatc cccgaaattc tacccaaatt   1860
gcttctgtct gttaaatgga attctagaga tgaagtagcc cagatgtatt gcttggtaaa   1920
agattggcct ccaatcaaac tgaacaggc tatggaactt ctggactgta attacccaga   1980
tcctatggtt cgaggttttg ctgttcggtg cttggaaaaa tatttaacag atgacaaact   2040
ttctcagtat ttaattcagc tagtacaggt cctaaaatat gaacaatatt tggataactt   2100
gcttgtgaga tttttactga agaaagcatt gactaatcaa aggattgggc acttttctt    2160 ttggcattta aaatctgaga tgcacaataa aacagttagc cagaggtttg gcctgctttt   2220
ggagtcctat tgtcgtgcat gtgggatgta tttgaagcac ctgaataggc aagtcgaggc   2280
aatggaaaag ctcattaact taactgacat tctcaaacag gagaagaagg atgaaacaca   2340
aaaggtacag atgaagtttt tagttgagca aatgaggcga ccagatttca tggatgctct   2400
acagggcttt ctgtctcctc taaaccctgc tcatcaacta ggaaacctca ggcttgaaga   2460
gtgtcgaatt atgtcctctg caaaaaggcc actgtggttg aattgggaga acccagacat   2520
catgtcagag ttactgtttc agaacaatga gatcatcttt aaaaatgggg atgatttacg   2580
gcaagatatg ctaacacttc aaattattcg tattatggaa aatatctggc aaaatcaagg   2640
tcttgatctt cgaatgttac cttatggttg tctgtcaatc ggtgactgtg tgggacttat   2700
tgaggtggtg cgaaattctc acactattat gcaaattcag tgcaaaggcg gcttgaaagg   2760
tgcactgcag ttcaacagcc acacactaca tcagtggctc aaagacaaga caaaggaga   2820 aatatatgat gcagccattg acctgtttac acgttcatgt gctggatact gtgtagctac   2880
cttcattttg ggaattggag atcgtcacaa tagtaacatc atggtgaaag acgatggaca   2940
actgtttcat atagatttttg gacactttttt ggatcacaag aagaaaaaat ttggttataa   3000
acgagaacgt gtgccatttg ttttgacaca ggatttctta atagtgatta gtaaaggagc   3060
ccaagaatgc acaaagacaa gagaatttga gaggtttcag gagatgtgtt acaaggctta   3120
tctagctatt cgacagcatg ccaatctctt cataaatctt ttctcaatga tgcttggctc   3180
```

```
tggaatgcca gaactacaat cttttgatga cattgcatac attcgaaaga ccctagcctt    3240
agataaaact gagcaagagg cttggagta tttcatgaaa caaatgaatg atgcacatca     3300
tggtggctgg acaacaaaaa tggattggat cttccacaca attaaacagc atgcattgaa    3360
ctgaaaagat aactgagaaa atgaaagctc actctggatt ccacactgca ctgttaataa    3420
ctctcagcag gcaaagaccg attgcatagg aattgcacaa tccatgaaca gcattagaat    3480
ttacagcaag aacagaaata aaatactata taatttaaat aatgtaaacg caaacagggt    3540
ttgatagcac ttaaactagt tcatttcaaa attaagcttt agaataatgc gcaatttcat    3600
gttatgcctt aagtccaaaa aggtaaactt tgaagattgt ttgtatcttt ttttaaaaaa    3660
caaaacaaaa caaaaatccc caaaatatat agaaatgatg gagaaggaaa aaaaaaaaa    3720 aaaa                                                                3724

<210> SEQ ID NO 9
<211> LENGTH: 21
<212> TYPE: RNA
<213> ORGANISM: artificial
<220> FEATURE:
<223> OTHER INFORMATION: sense strand polynucleotide

<400> SEQUENCE: 9
ggaaauaugg cuucucugau u                                              21

<210> SEQ ID NO 10
<211> LENGTH: 21
<212> TYPE: RNA
<213> ORGANISM: artificial
<220> FEATURE:
<223> OTHER INFORMATION: sense strand polynucleotide

<400> SEQUENCE: 10
gaaagacgag agaccaauau u                                              21

<210> SEQ ID NO 11
<211> LENGTH: 21
<212> TYPE: RNA
<213> ORGANISM: artificial
<220> FEATURE:
<223> OTHER INFORMATION: sense strand polynucleotide

<400> SEQUENCE: 11
guaaagcauu gugucauaau u                                              21

<210> SEQ ID NO 12
<211> LENGTH: 21
<212> TYPE: RNA
<213> ORGANISM: artificial
<220> FEATURE:
<223> OTHER INFORMATION: sense strand polynucleotide

<400> SEQUENCE: 12
uggcuucucu gacccauuau u                                              21

<210> SEQ ID NO 13
<211> LENGTH: 19
<212> TYPE: RNA
<213> ORGANISM: artificial
<220> FEATURE:
<223> OTHER INFORMATION: sense strand polynucleotide

<400> SEQUENCE: 13
auguuuacua ccaaaugga                                                 19
```

<210> SEQ ID NO 14
<211> LENGTH: 19
<212> TYPE: RNA
<213> ORGANISM: artificial
<220> FEATURE:
<223> OTHER INFORMATION: sense strand polynucleotide

<400> SEQUENCE: 14
aacuagaagu auguugcua                                                    19

<210> SEQ ID NO 15
<211> LENGTH: 19
<212> TYPE: RNA
<213> ORGANISM: artificial
<220> FEATURE:
<223> OTHER INFORMATION: sense strand polynucleotide

<400> SEQUENCE: 15
aauggcuuug aaucuuugg                                                    19

<210> SEQ ID NO 16
<211> LENGTH: 19
<212> TYPE: RNA
<213> ORGANISM: artificial
<220> FEATURE:
<223> OTHER INFORMATION: sense strand polynucleotide

<400> SEQUENCE: 16
cugaagaaag cauugacua                                                    19

<210> SEQ ID NO 17
<211> LENGTH: 1446
<212> TYPE: DNA
<213> ORGANISM: Homo sapiens

<400> SEQUENCE: 17
atgaatgagg tgtctgtcat caaagaaggc tggctccaca agcgtggtga atacatcaag        60
acctggaggc cacggtactt cctgctgaag agcgacggct ccttcattgg gtacaaggag       120
aggcccgagg cccctgatca gactctaccc cccttaaaca acttctccgt agcagaatgc       180
cagctgatga gaccgagag gccgcgaccc aacacctttg tcatacgctg cctgcagtgg       240
accacagtca tcgagaggac cttccacgtg gattctccag acgagaggga ggagtggatg       300
cgggccatcc agatggtcgc caacagcctc aagcagcggg ccccaggcga ggaccccatg       360
gactacaagt gtggctcccc cagtgactcc tccacgactg aggagatgga agtggcggtc       420
agcaaggcac gggctaaagt gaccatgaat gacttcgact atctcaaact ccttggcaag       480
ggaacctttg gcaaagtcat cctggtgcgg gagaaggcca ctggccgcta ctacgccatg       540
aagatcctgc ggaaggaagt catcattgcc aaggatgaag tcgctcacac agtcaccgag       600
agccgggtcc tccagaacac caggcacccg ttcctcactg cgctgaagta tgccttccag       660
acccacgacc gcctgtgctt tgtgatggag tatgccaacg ggggtgagct gttcttccac       720
ctgtcccggg agcgtgtctt cacagaggag cgggcccggt tttatggtgc agagattgtc       780
tcggctcttg agtacttgca ctcgcgggac gtggtatacc gcgacatcaa gctggaaaac       840
ctcatgctgc acaagatgg ccacatcaag atcactgact ttggcctctg caaagagggc       900
atcagtgacg gggccaccat gaaaaccttc tgtgggaccc ggagtacct ggcgcctgag       960 gtgctggagg acaatgacta tggccgggcc gtggactggt ggggctggg tgtggtcatg      1020 tacgagatga tgtgcggccg cctgcccttc tacaaccagg accacgagcg cctcttcgag      1080

```
ctcatcctca tggaagagat ccgcttcccg cgcacgctca gccccgaggc caagtccctg   1140
cttgctgggc tgcttaagaa ggaccccaag cagaggcttg gtgggggcc cagcgatgcc    1200 aaggaggtca tggagcacag gttcttcctc agcatcaact ggcaggacgt ggtccagaag   1260
aagctcctgc caccttcaa acctcaggtc acgtccgagg tcgacacaag gtacttcgat    1320
gatgaattta ccgcccagtc catcacaatc acacccctg accgctatga cagcctgggc    1380
ttactggagc tggaccagcg gacccacttc ccccagttct cctactcggc cagcatccgc   1440
gagtga                                                              1446
```

<210> SEQ ID NO 18
<211> LENGTH: 481
<212> TYPE: PRT
<213> ORGANISM: Homo sapiens

<400> SEQUENCE: 18

```
Met Asn Glu Val Ser Val Ile Lys Glu Gly Trp Leu His Lys Arg Gly
  1               5                  10                  15

Glu Tyr Ile Lys Thr Trp Arg Pro Arg Tyr Phe Leu Leu Lys Ser Asp
             20                  25                  30

Gly Ser Phe Ile Gly Tyr Lys Glu Arg Pro Glu Ala Pro Asp Gln Thr
         35                  40                  45

Leu Pro Pro Leu Asn Asn Phe Ser Val Ala Glu Cys Gln Leu Met Lys
     50                  55                  60

Thr Glu Arg Pro Arg Pro Asn Thr Phe Val Ile Arg Cys Leu Gln Trp
 65                  70                  75                  80

Thr Thr Val Ile Glu Arg Thr Phe His Val Asp Ser Pro Asp Glu Arg
                 85                  90                  95

Glu Glu Trp Met Arg Ala Ile Gln Met Val Ala Asn Ser Leu Lys Gln
            100                 105                 110

Arg Ala Pro Gly Glu Asp Pro Met Asp Tyr Lys Cys Gly Ser Pro Ser
        115                 120                 125

Asp Ser Ser Thr Thr Glu Glu Met Glu Val Ala Val Ser Lys Ala Arg
    130                 135                 140

Ala Lys Val Thr Met Asn Asp Phe Asp Tyr Leu Lys Leu Leu Gly Lys
145                 150                 155                 160

Gly Thr Phe Gly Lys Val Ile Leu Val Arg Glu Lys Ala Thr Gly Arg
                165                 170                 175

Tyr Tyr Ala Met Lys Ile Leu Arg Lys Glu Val Ile Ile Ala Lys Asp
            180                 185                 190

Glu Val Ala His Thr Val Thr Glu Ser Arg Val Leu Gln Asn Thr Arg
        195                 200                 205

His Pro Phe Leu Thr Ala Leu Lys Tyr Ala Phe Gln Thr His Asp Arg
    210                 215                 220

Leu Cys Phe Val Met Glu Tyr Ala Asn Gly Gly Glu Leu Phe Phe His
225                 230                 235                 240

Leu Ser Arg Glu Arg Val Phe Thr Glu Glu Arg Ala Arg Phe Tyr Gly
                245                 250                 255

Ala Glu Ile Val Ser Ala Leu Glu Tyr Leu His Ser Arg Asp Val Val
            260                 265                 270

Tyr Arg Asp Ile Lys Leu Glu Asn Leu Met Leu Asp Lys Asp Gly His
        275                 280                 285

Ile Lys Ile Thr Asp Phe Gly Leu Cys Lys Glu Gly Ile Ser Asp Gly
    290                 295                 300
```

```
Ala Thr Met Lys Thr Phe Cys Gly Thr Pro Glu Tyr Leu Ala Pro Glu
305                 310                 315                 320

Val Leu Glu Asp Asn Asp Tyr Gly Arg Ala Val Asp Trp Trp Gly Leu
                325                 330                 335

Gly Val Val Met Tyr Glu Met Met Cys Gly Arg Leu Pro Phe Tyr Asn
            340                 345                 350

Gln Asp His Glu Arg Leu Phe Glu Leu Ile Leu Met Glu Glu Ile Arg
        355                 360                 365

Phe Pro Arg Thr Leu Ser Pro Glu Ala Lys Ser Leu Leu Ala Gly Leu
    370                 375                 380

Leu Lys Lys Asp Pro Lys Gln Arg Leu Gly Gly Gly Pro Ser Asp Ala
385                 390                 395                 400

Lys Glu Val Met Glu His Arg Phe Phe Leu Ser Ile Asn Trp Gln Asp
                405                 410                 415

Val Val Gln Lys Lys Leu Leu Pro Pro Phe Lys Pro Gln Val Thr Ser
            420                 425                 430

Glu Val Asp Thr Arg Tyr Phe Asp Asp Glu Phe Thr Ala Gln Ser Ile
        435                 440                 445

Thr Ile Thr Pro Pro Asp Arg Tyr Asp Ser Leu Gly Leu Leu Glu Leu
    450                 455                 460

Asp Gln Arg Thr His Phe Pro Gln Phe Ser Tyr Ser Ala Ser Ile Arg
465                 470                 475                 480

Glu

<210> SEQ ID NO 19
<211> LENGTH: 5263
<212> TYPE: DNA
<213> ORGANISM: Homo sapiens

<400> SEQUENCE: 19 cgggggggc cgcgccgtgc tagccgttgg gcctgcctcg gaggaggcgt cgccgccgcc      60
gctgccgctg ccggcgccgt tgccgctgcc gggaaacaca aggaaaggga accagcgcag    120
cgtggcgatg ggcgggggta gagccccgcc ggagaggctg ggcggctgcc ggtgacagac    180
tgtgccctgt ccacggtgcc tcctgcatgt cctgctgccc tgagctgtcc cgagctaggt    240
gacagcgtac cacgctgcca ccatgaatga ggtgtctgtc atcaaagaag ctggctcca    300 caagcgtggt gaatacatca gacctggag gccacggtac ttcctgctga gagcgacgg     360 ctccttcatt gggtacaagg agaggcccga ggccctgat cagactctac cccccttaaa    420
caacttctcc gtagcagaat gccagctgat gaagaccgag aggccgcgac ccaacacctt    480
tgtcatacgc tgcctgcagt ggaccacagt catcgagagg accttccacg tggattctcc    540
agacgagagg gaggagtgga tgcgggccat ccagatggtc gccaacagcc tcaagcagcg    600
ggccccaggc gaggacccca tggactacaa gtgtggctcc cccagtgact cctccacgac    660
tgaggagatg gaagtggcgg tcagcaaggc acgggctaaa gtgaccatga atgacttcga    720
ctatctcaaa ctccttggca agggaacctt tggcaaagtc atcctggtgc gggagaaggc    780
cactggccgc tactacgcca tgaagatcct gcggaaggaa gtcatcattg ccaaggatga    840
agtcgctcac acagtcaccg agagccgggt cctccagaac accaggcacc cgttcctcac    900
tgcgctgaag tatgccttcc agacccacga ccgcctgtgc tttgtgatgg agtatgccaa    960
cgggggtgag ctgttcttcc acctgtcccg ggagcgtgtc ttcacagagg agcgggcccg   1020
gttttatggt gcagagattg tctcggctct tgagtacttg cactcgcggg acgtggtata   1080
ccgcgacatc aagctggaaa acctcatgct ggacaaagat ggccacatca agatcactga   1140
```

```
ctttggcctc tgcaaagagg gcatcagtga cggggccacc atgaaaacct tctgtgggac    1200
cccggagtac ctggcgcctg aggtgctgga ggacaatgac tatggccggg ccgtggactg    1260 gtggggctg ggtgtggtca tgtacgagat gatgtgcggc cgcctgccct tctacaacca    1320
ggaccacgag cgcctcttcg agctcatcct catggaagag atccgcttcc cgcgcacgct    1380
cagccccgag gccaagtccc tgcttgctgg gctgcttaag aaggacccca agcagaggct    1440
tggtgggggg cccagcgatg ccaaggaggt catggagcac aggttcttcc tcagcatcaa    1500
ctggcaggac gtggtccaga agaagctcct gccaccctto aaacctcagg tcacgtccga    1560
ggtcgacaca aggtacttcg atgatgaatt taccgcccag tccatcacaa tcacaccccc    1620
tgaccgctat gacagcctgg gcttactgga gctggaccag cggacccact tcccccagtt    1680
ctcctactcg gccagcatcc gcgagtgagc agtctgccca cgcagaggac gcacgctcgc    1740
tgccatcacc gctgggtggt ttttccccc taacttttta cttagccttt ttggtttgtg    1800
tccccacccc cacctcctca cccccttccc agttcttctt caggcccctc ccagacgcac    1860
cccagcggcc cctgcagccc ctgcctccag cctccagcct caccttttgtg cccagactcg    1920 catttggaag actccacctc ccgcccaggc ctgggctgtt gggcggttgg agattcaggt    1980
tttaatccac acaagcccca gtgaggggtg aagcatggcg cctggggcct gcctgagttt    2040
ctggcctggg tgtcgtgctg gtgtctgcct ccgcgctgct gcatctggac gaaggctgcc    2100
ttctggtggg acgcgacacc cggcagacag tggtgctgcc ttccaggccc cgtggcctag    2160
gctcggagtg gccaggcacg gggcggtcca atccccacc cgctgtcccc ctatggggc    2220 agaaaagcaa taatgtccag gggcaggcag gggcccttgg gagctgcagg gctggggtt    2280 agggctgctc cctggtgaat ggagtcgat cctaggatct gtaccatggg gaaccaggag    2340
tggccgggct gggtgccgcc tcctggtccg gcctcctccc caccaaactg tcctcaccct    2400
atggatgagg caggaggaac atttggggcc aaacctgcct gcctcccagc cccgtgcctt    2460
actagggctt ccttccagct ggccttacct cccgctggac cctgggcctg gcctggcccc    2520
actgggggct atgggctggg ctcaccctct cctctgcggg ggtggagggc caccagcctt    2580
ggctgttaca atcttacacc ggacagtatt gggcccatg gacttggtca gggaggggtg    2640 gggtgggca tctctggtac ctattgggt ggggggcctc tgaaaaggga ggctcctagg    2700 ccccctcac ccctccctct ccccagggcc ccacgttctg cagccttaag gttgaacatg    2760
agtgcacgtc catgtcagtg ctgtgggact cctgtgcgtg cctcggactg cgtgtgtcgg    2820
cgggacgcag gcacgtgg gtgtgtgtgc atgtgtgttt gtgtgagggc agcgtgtcct    2880
ccagtgtgca tggtgtgtgg gcttgggccc catccctggc ccgagcattt catcctgtgg    2940
gggaggggtg ctgacctagt gggaggagcc ccactgtgat ccatgagctg ccctgcccac    3000
gcctcccctc cctgtagcaa cacctctggg tgttttggagt ttagcttttg tgggtttgct    3060
ctccctatcc catctcctgt actacacagt tcatggcagg gtggggaggg gtggggttgg    3120
ttcgggtggg tgagggtctt tttcctctgt gtgcgatgtt gttatctgac agttctccgt    3180
ccctactggc ctttctcctc gtcttcatat ttgtacggta caagcaataa agacactcat    3240
ttcagaccag ggcccagcct gcactcacgc cagcccaacc actctgggct ttgccttggt    3300
gatggagtca gaccccctggg ccccagctcc tcctgtacta gccgttccct tcagcaagga    3360
gggcactgag ctcagggtga gggcagctgg ggtgtgtgca ggagctcagg ctggagaggg    3420
tgggtggagc tggtgctgtg gggctgaggg gtatgggaag gctccccgca tgtggggtg    3480 gggtggacag agaccactcc aggccctcag tgctgcttag gctaagagag gtggggtgga    3540
```

```
gggacagggc tggaagatct gggtagccca gaatgaggag ggtgcctgtg ctgtcactga    3600
atgagaggga gtggttcatt ccacccggct gccgagcctc agaggggggc attcctatcc    3660
tgccccacct ccctgtttat gctgccacct ggaagccttg aggcccccaa attccagtac    3720
agacccagtg gtgtgttcat ggtggcgtgg ttgctgtcac ctgggagctc ctgagcgttt    3780
ggttagaacc ctgttcagct tggggtcagc cctcccctag tcactgccct ttagcctgga    3840
tgtgtctggg cccctgcact tcccgtgctt gagtcacgtg gctgcatggc cgggcgctgg    3900
ccggatggaa cacctccccc agcaagggac cagggaccag agccctggcc tgccctgctg    3960
agccctgctg tgcagagggc ctggcacaga tgaatttgag attttgccgc aaggtgttag    4020
cacttcacac ccattgagtc tttgagattt taagtgaatg taagcagaaa aagtcagatc    4080
caatttacag aaatcagagt tagctacagc taggactcgt ttggttgggg ttttttagtt    4140
tgtctttcta aagtcatgtg gaccttaatt taattacaaa agtctaccct ggtggtcata    4200
aaataggcag gcctatgaag aaaggccttt tactcttcca tctcatccca gccccgagtt    4260
gacccacgtt gctgctcctc acaccatggt gatgcaggtc tcgtagtgtg ggcacaggcc    4320
tggctacctc atctttttag tgcctctctc ctcttccaca ggatgggtc ccacagctgc    4380 agcagctggc cccgtagttg agcatgtgtg gttatcctgt agagcttttc ccaagaaggg    4440
tgtttgaact tagagtctta ataaaatctt accaaataaa ttttgagtag aataatcgtc    4500
ttttgcaatg tacattttaa aaatttcaca cattcttttt tgtatataaa gaacagtgac    4560
tgggcacagt ggctcatgcc tgtaatccca gcaatttggg aggccgaggc gggcgggtct    4620
cttgaggcca ggggttcgag accagcctgg gcatcatagg gagaccttca tctctacaaa    4680
aaatacaaaa attagctggg catggtggtg catgcctgca atcccagcta acttggaagg    4740
ctgaggtgag gtgggaagat cacttgagcc caggagtttg aggctgcagt gagctatgat    4800
tgcggcactg cactgcagcc tgggacaatg agactgtgtc tctaaaaata aaaaaaaaa    4860 aaacatgata catgctatta aaaagacag caaagcagga gtataagaaa ggaaattcac    4920
ccgaggtcgc agggccttga gtactcattt tggtgctgat tacctctctg caaatggaca    4980
cggcatcata aattggtagt ttcctgctct tttgtgtaa tctttccag ttaatgtgaa    5040 gcctctgggg gctgccctcg tgcactgatg gttgtgtgga gtcggggggcg gcagtgcgat    5100 tccctttag ctgctgcatg gggggaactc aggctttcca gctgcttcct ggggttccat    5160
ggggtagacc cctcaaccgc ttcagctgcc ccgttaacag gaattgactt ggtttcgttt    5220
ggtgctacca gcagtcctgt aataaactag ctatccatct gta                     5263
```

<210> SEQ ID NO 20  
<211> LENGTH: 19  
<212> TYPE: RNA  
<213> ORGANISM: artificial  
<220> FEATURE:  
<223> OTHER INFORMATION: sense strand polynucleotide

<400> SEQUENCE: 20

```
guacuucgau gaugaauuu                                                    19
```